United States Patent
Bence et al.

(10) Patent No.: US 10,335,411 B2
(45) Date of Patent: Jul. 2, 2019

(54) ADMINISTRATION OF UBIQUITIN-ACTIVATING ENZYME INHIBITOR AND RADIATION

(71) Applicant: Millennium Pharmaceuticals, Inc., Cambridge, MA (US)

(72) Inventors: Neil Bence, Belmont, CA (US); Marc Hyer, Swampscott, MA (US); Michael Milhollen, Foxborough, MA (US); Vivek Samnotra, Concord, MA (US); Sergio Luis Santillana Soto, Lexington, MA (US); Darshan Sappal, Malden, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/522,717

(22) PCT Filed: Oct. 23, 2015

(86) PCT No.: PCT/US2015/057064
§ 371 (c)(1),
(2) Date: Apr. 27, 2017

(87) PCT Pub. No.: WO2016/069393
PCT Pub. Date: May 6, 2016

(65) Prior Publication Data
US 2017/0333434 A1 Nov. 23, 2017

Related U.S. Application Data
(60) Provisional application No. 62/072,299, filed on Oct. 29, 2014, provisional application No. 62/199,011, filed on Jul. 30, 2015.

(51) Int. Cl.
| | | |
|---|---|---|
| *A61N 5/10* | (2006.01) | |
| *A61K 41/00* | (2006.01) | |
| *A61P 35/00* | (2006.01) | |
| *A61K 31/519* | (2006.01) | |

(52) U.S. Cl.
CPC ........ *A61K 31/519* (2013.01); *A61K 41/0038* (2013.01); *A61N 5/1077* (2013.01); *A61P 35/00* (2018.01); *A61N 2005/1098* (2013.01)

(58) Field of Classification Search
CPC ... A61K 31/519; A61N 5/1077; A61N 5/1007
USPC ...................................................... 514/233.2
See application file for complete search history.

(56) References Cited

U.S. PATENT DOCUMENTS
| | | | | |
|---|---|---|---|---|
| 9,290,500 B2 * | 3/2016 | Afroze | ............. | C07D 487/04 |
| 2009/0036678 A1 | 2/2009 | Armitage et al. | | |
| 2012/0322791 A1 | 12/2012 | Siddiqui et al. | | |
| 2013/0150362 A1 | 6/2013 | Zhao et al. | | |
| 2013/0217682 A1 | 8/2013 | Afroze et al. | | |
| 2014/0088096 A9 | 3/2014 | Afroze et al. | | |

FOREIGN PATENT DOCUMENTS
| | | | |
|---|---|---|---|
| WO | WO 2013/123169 A1 | 8/2013 | |
| WO | WO 2016/069393 A1 | 5/2016 | |

OTHER PUBLICATIONS

Beers et al., The Merck Index, 2nd Edition, "Radiation Therapy", p. 1043 (2003).*
International Search Report; International Application No. PCT/US2015/057064; dated Mar. 21, 2016.
Schulman, B.A., and Harper, J.W., "Ubiquitin-like protein activation by E1 enzymes: the apex for downstream signalling pathways," *Nat Rev Mol Cell Biol* 10:319-331, Macmillan Publishers Limited, United Kingdom (2009).
Deshaies, R.J., and Joazeiro, C.A., "RING domain E3 ubiquitin ligases," *Annu Rev Biochem* 78:399-434, Annual Reviews, United States (2009).
Lipkowitz, S., and Weissman, A.M., "RINGs of good and evil: RING finger ubiquitin ligases at the crossroads of tumour suppression and oncogenesis," *Nat Rev Cancer* 11.629-643, Macmillan Publishers Limited, United Kingdom (2011).
Rotin, D., and Kumar, S., "Physiological functions of the HECT family of ubiquitin ligases," *Nat Rev Mol Cell Biol* 10:398-409, Macmillan Publishers Limited, United Kingdom (2009).
Jin, J., et al., "Dual E1 activation systems for ubiquitin differentially regulate E2 enzyme charging," *Nature* 447:1135-1138, Nature Publishing Group, United States (2007).
Ciechanover, A., et al., "Ubiquitin dependence of selective protein degradation demonstrated in the mammalian cell cycle mutant ts85," *Cell* 37:57-66, MIT, United States (1984).
Finley, D., et al., "Thermolability of ubiquitin-activating enzyme from the mammalian cell cycle mutant ts85," *Cell* 37:43-55, MIT, United States (1984).
Chandrasekharan, M.B., et al., "Histone H2B ubiquitination and beyond: Regulation of nucleosome stability, chromatin dynamics and the trans-histone H3 methylation," *Epigenetics* 5:460-468, Landes Bioscience, United States (2010).
Trotman, L.C., et al., "Ubiquitination regulates PTEN nuclear import and tumor suppression," *Cell* 128:141-156, Elsevier Inc., Netherlands (2007).
Gregory, R.C., et al., "Regulation of the Fancomi anemia pathway by monoubiquitin," *Semin Cancer Biol* 13:77-82, Elsevier Science Ltd, Netherlands (2003).
Mosesson, Y., and Yarden, Y., "Monoubiquitylation: a recurrent theme in membrane protein transport," *Isr Med Assoc J* 8:233-237, Israel Medical Association, Israel (2006).

(Continued)

Primary Examiner — Kevin E Weddington
(74) Attorney, Agent, or Firm — Sterne, Kessler, Goldstein & Fox P.L.L.C.

(57) ABSTRACT

Disclosed are methods for the treatment of cancer in patients in need of such treatment. The methods comprise administering to such a patient an ubiquitin-activating enzyme (UAE) inhibitor such as ((1R,2R,3S,4R)-2,3-dihydroxy-4-(2-(3-(trifluoromethylthio) phenyl)pyrazolo[1,5-a]pyrimidin-7-ylamino)cyclopentyl)methyl sulfamate (Compound 1) or a pharmaceutically acceptable salt in combination with radiation. Also disclosed are medicaments for use in the treatment of cancer.

20 Claims, 12 Drawing Sheets

(56) References Cited

OTHER PUBLICATIONS

Behrends, C., and Harper, J.W., "Constructing and decoding unconventional ubiquitin chains," *Nat Struct Mol Biol* 18:520-528, Nature America, Inc., United States (2011).

Bennett, E.J., and Harper, J.W., "DNA damage: ubiquitin marks the spot," *Nat Struct Mol Biol* 15:20-22, Nature Publishing Group, United States (2008).

Komander, D., "The emerging complexity of protein ubiquitination," *Biochem Soc Trans* 37:937-953, Biochemical Society, United Kingdom (2009).

Xu, W.G., et al., "The ubiquitin-activating enzyme E1 as a therapeutic target for the treatment of leukemia and multiple myeloma," *Blood*, 115:2251-59, The American Society of Hematology, United States (2010).

Hartmann, J.T., and Lipp, H-P., "Toxicity of platinum compounds," *Exper. Opin. Pharmacother.* 4(6) 889-901, Ashley Publications, United Kingdom (2003).

Armitage, I., et al., N-(tert-Butoxycarbonyl)-N-[(triethylenediammonium)sulfonyl]-azanide: A Convenient Sulfamoylation Reagent for Alcohols *Org. Lett.*; 14, 2626-2629,, American Chemical Society, United States (2012).

Saksena, A. K., "A Convenient Route to Carbocyclic Analogs of Nucleosides: (±) Aristeromycin," *Tetrahedron Lett*, 21, 133-136, Pergamon Press Ltd., Great Britain (1980).

Hutchinson, E. J., et al., "Stereospecific synthesis of 1,9-bis(β-D-glycosyl)adenines: a chemical route to stable analogues of cyclic-ADP ribose (cADPR)," *J. Chem. Soc., Chem. Commun.* 1859-1860, Royal Society of Chemistry, United Kingdom (1997).

Tokoro, Y. and Kobayashi, Y., "Realisation of highly stereoselective dihydroxylation of a cyclopentene in the synthesis of (-)-aristeromycin," *Chem. Commun*, 807-809, Royal Society of Chemistry, United Kingdom (1999).

Dominguez, B. M. and Cullis, P. M., "2-Azabicyclo[2.2.1]hept-5-en-3-one Epoxide: A Versatile Intermediate for the Synthesis of Cyclopentyl Carbocyclic 2-Deoxy-, 3-Deoxy- & Ara- Ribonucleoside Analogues," *Tetrahedron Lett.*, 40, 5783-5786, Elsevier Science Ltd., Netherlands (1999).

PubChem compound database, "Tak-243", CID: 71715374, accessed at https://pubchem.ncbi.nlm.nih.gov, accessed on Jun. 13, 2018.

Extended European Search Report of European Application No. 15854199.5, European Patent Office, Munich, Germany, dated Jun. 25, 2018, 7 pages.

\* cited by examiner

Figure 1a: The anti-tumor activity of Compound 1 at 15 mg/kg and Radiation in the HN-13-0014 xenograft model
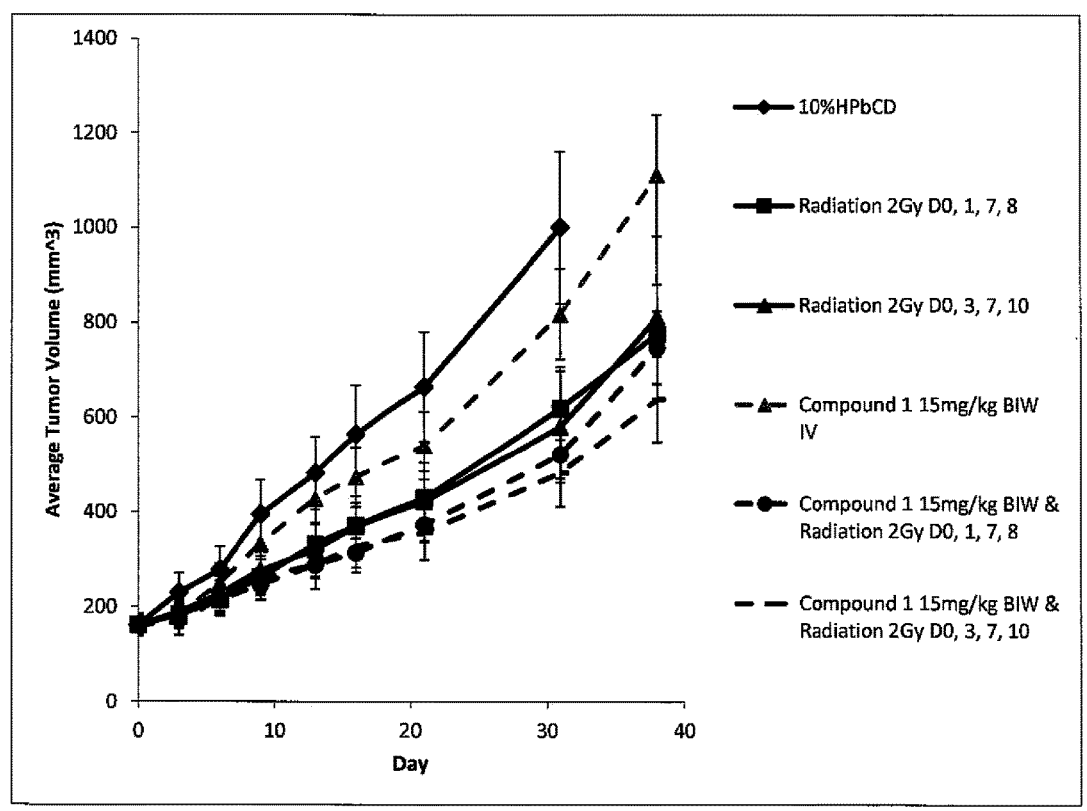

Figure 1b: The anti-tumor activity of Compound 1 at 6.25 mg/kg and Radiation in the HN-13-0014 xenograft model
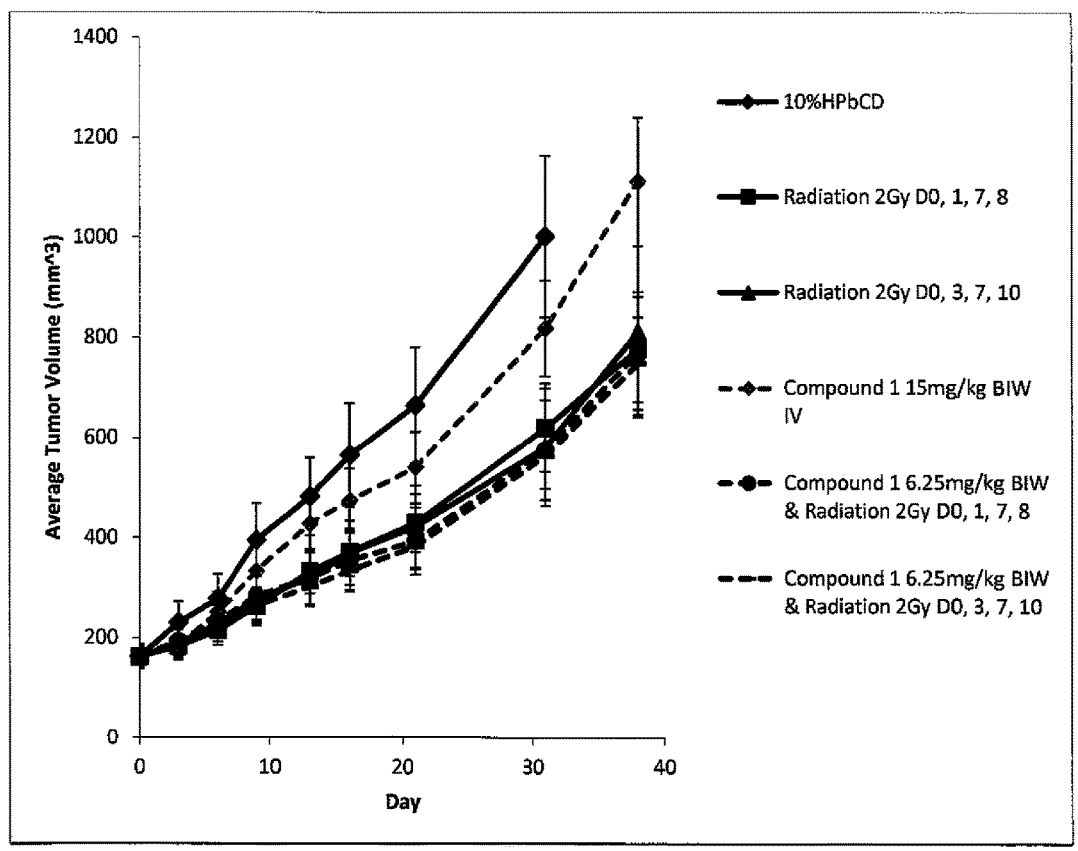

Figure 2a: The anti-tumor activity of Compound 1 at 15 mg/kg and Radiation in the first study using the LU-01-0030 xenograft model
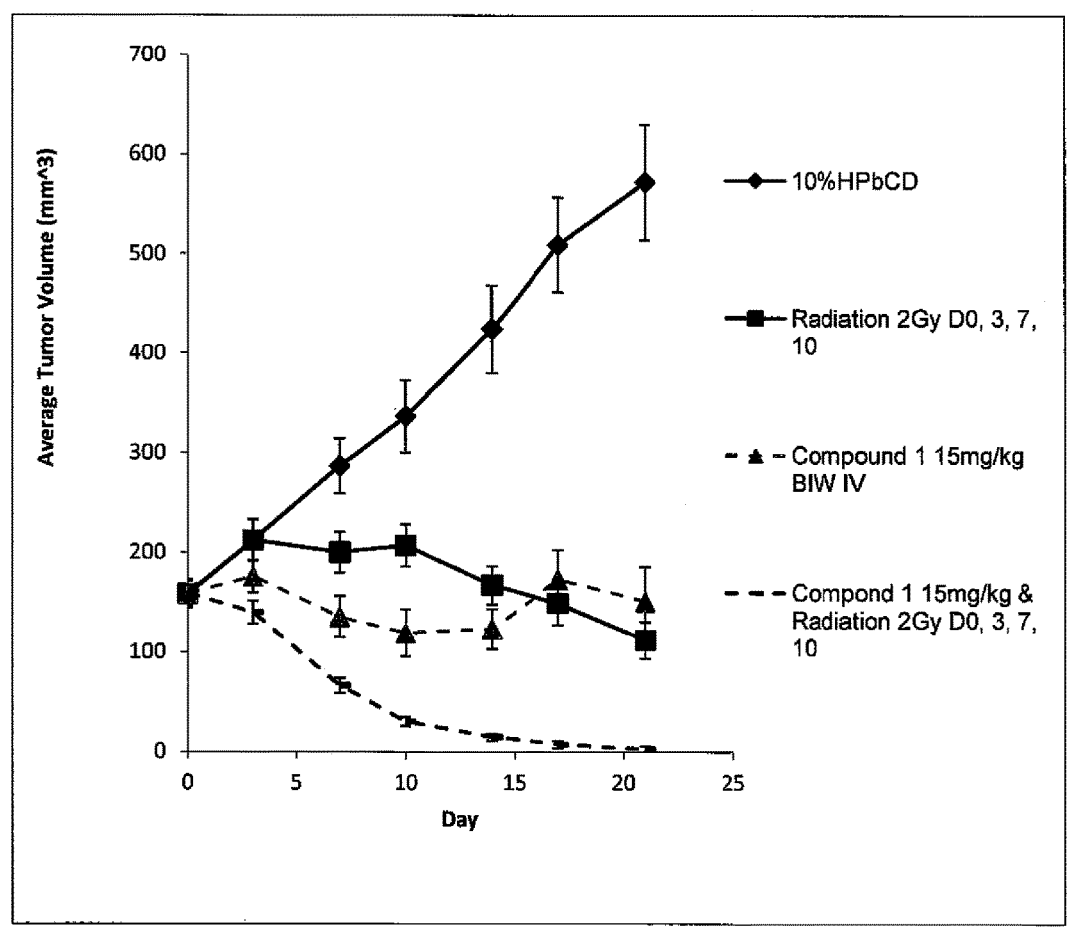

Figure 2b: The anti-tumor activity of Compound 1 at 15 mg/kg and Radiation in the first study using the LU-01-0030 xenograft model
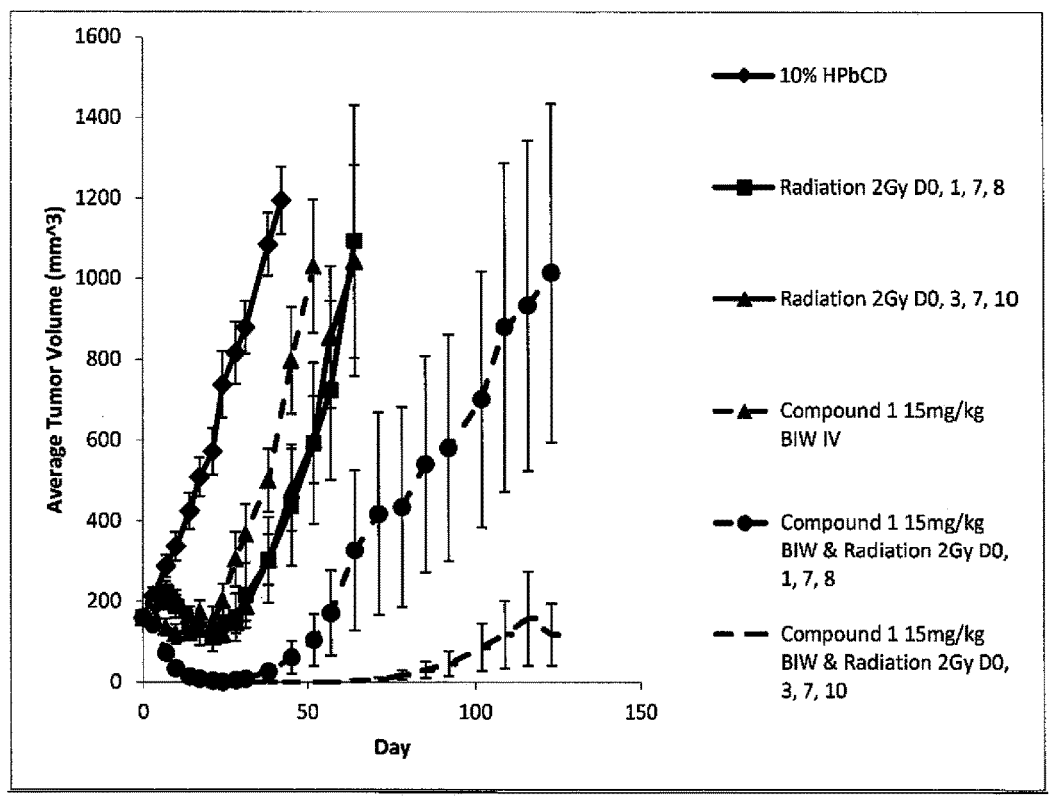

Figure 2c: The anti-tumor activity of Compound 1 at 6.25 mg/kg and Radiation in the first study using the LU-01-0030 xenograft model
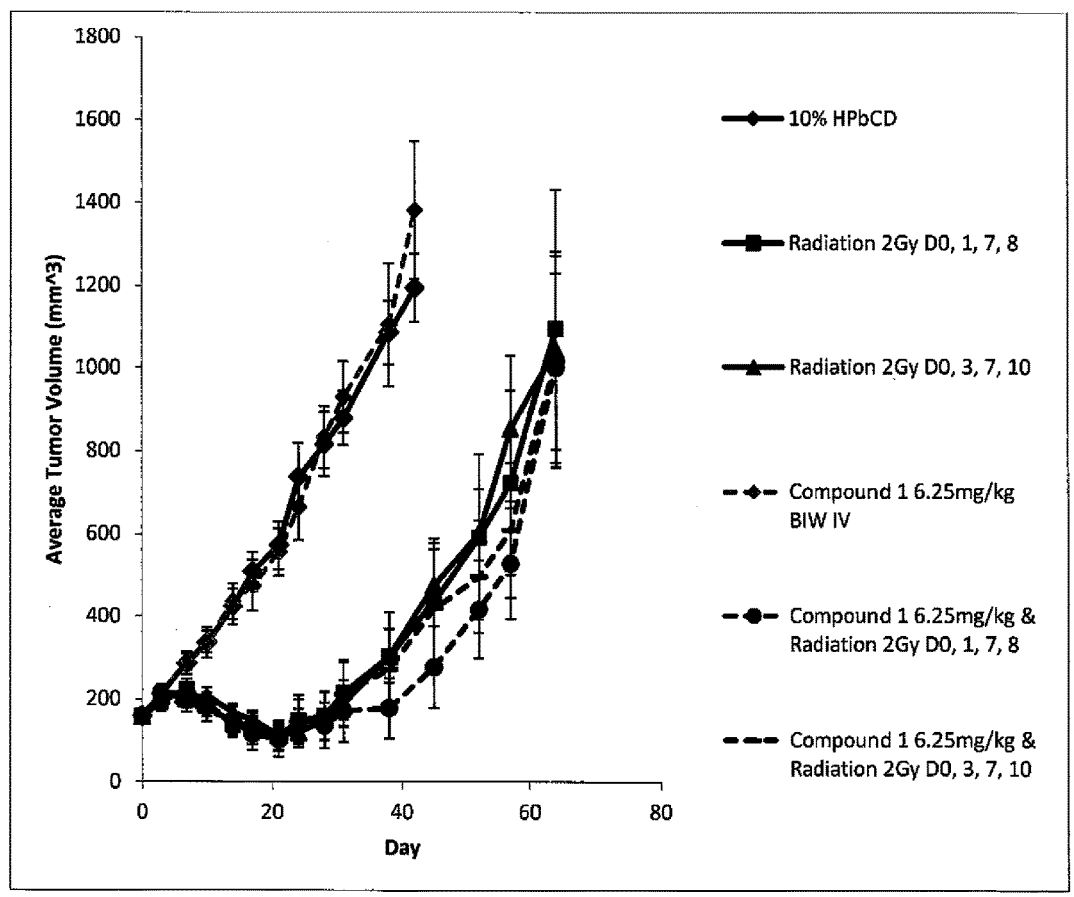

Figure 3a: The anti-tumor activity of Compound 1 at 15 mg/kg and Radiation in the LU-01-0266 xenograft model
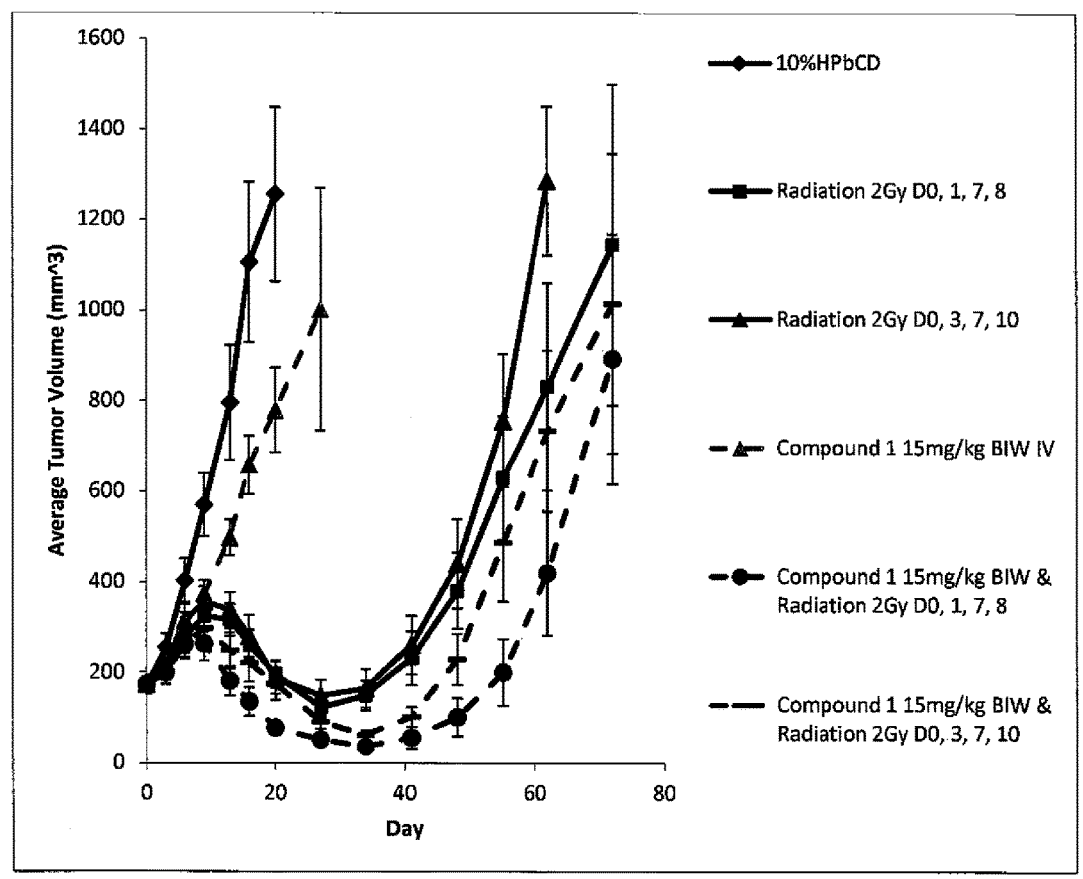

Figure 3b: The anti-tumor activity of Compound 1 at 6.25 mg/kg and Radiation in the LU-01-0266 xenograft model
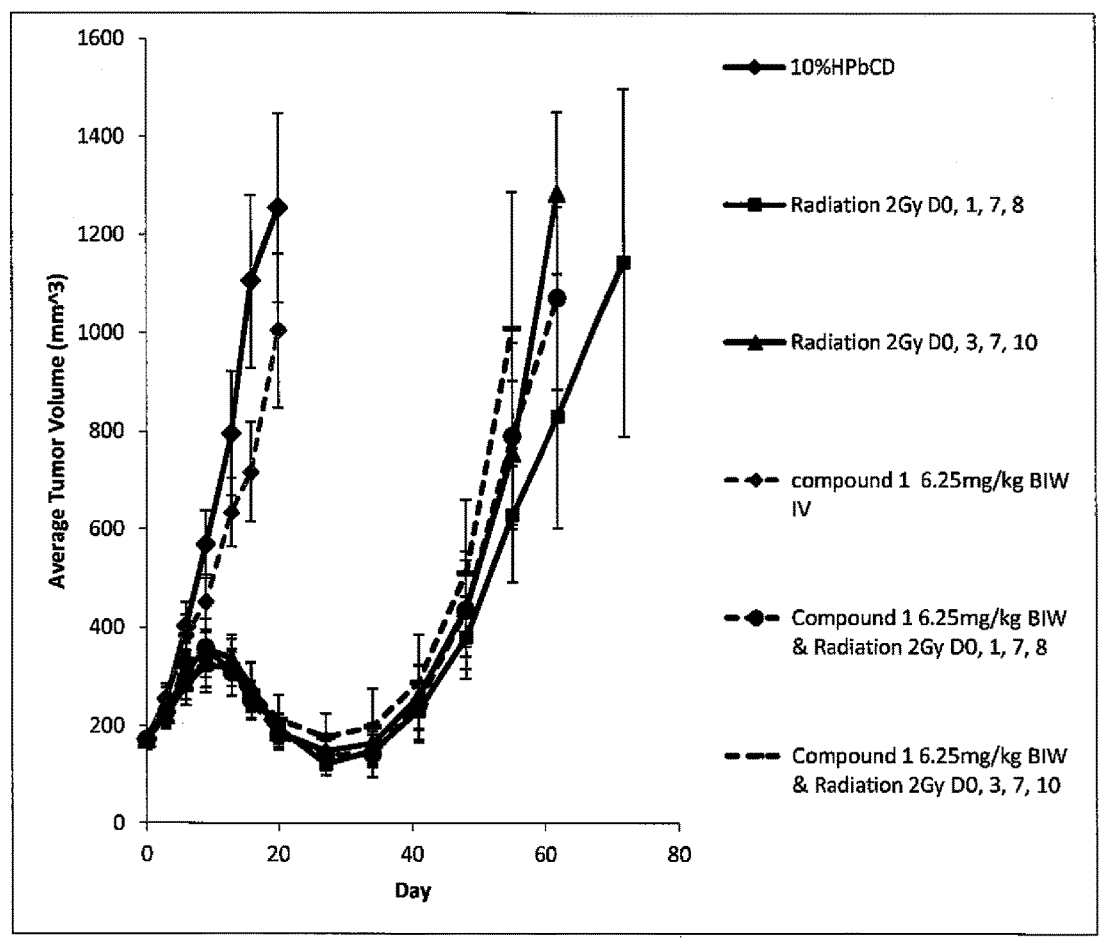

Figure 4a: The anti-tumor activity of Compound 1 at 15 mg/kg and Radiation in the ST-02-0004 xenograft model
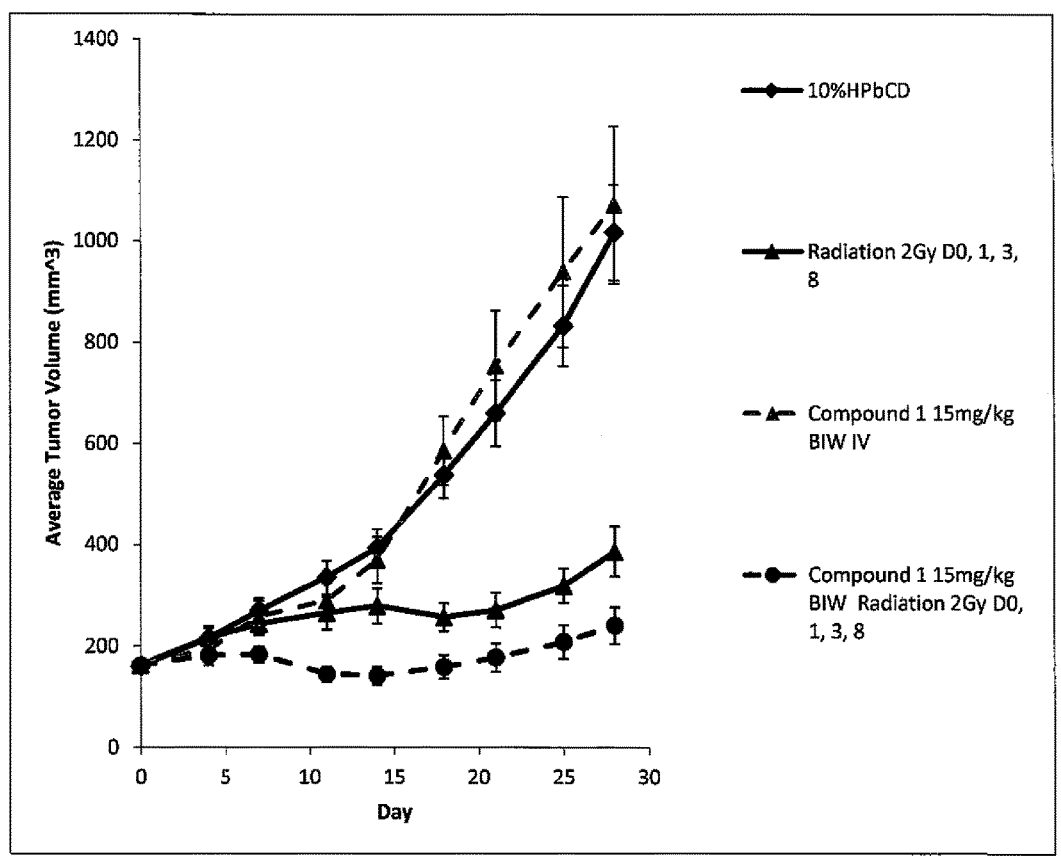

Figure 4b: The anti-tumor activity of Compound 1 at 6.25 mg/kg and Radiation in the ST-02-0004 xenograft model
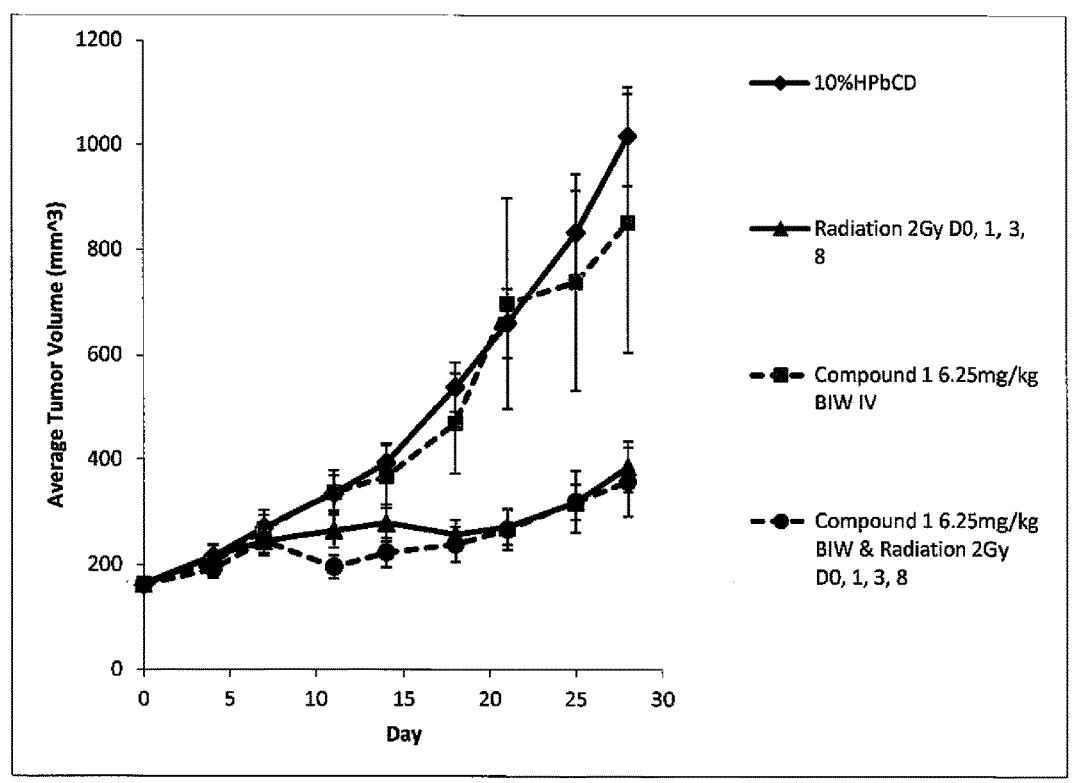

Figure 5a: The anti-tumor activity of Compound 1 at 15mg/kg and Radiation in the HN-13-0007 xenograft model
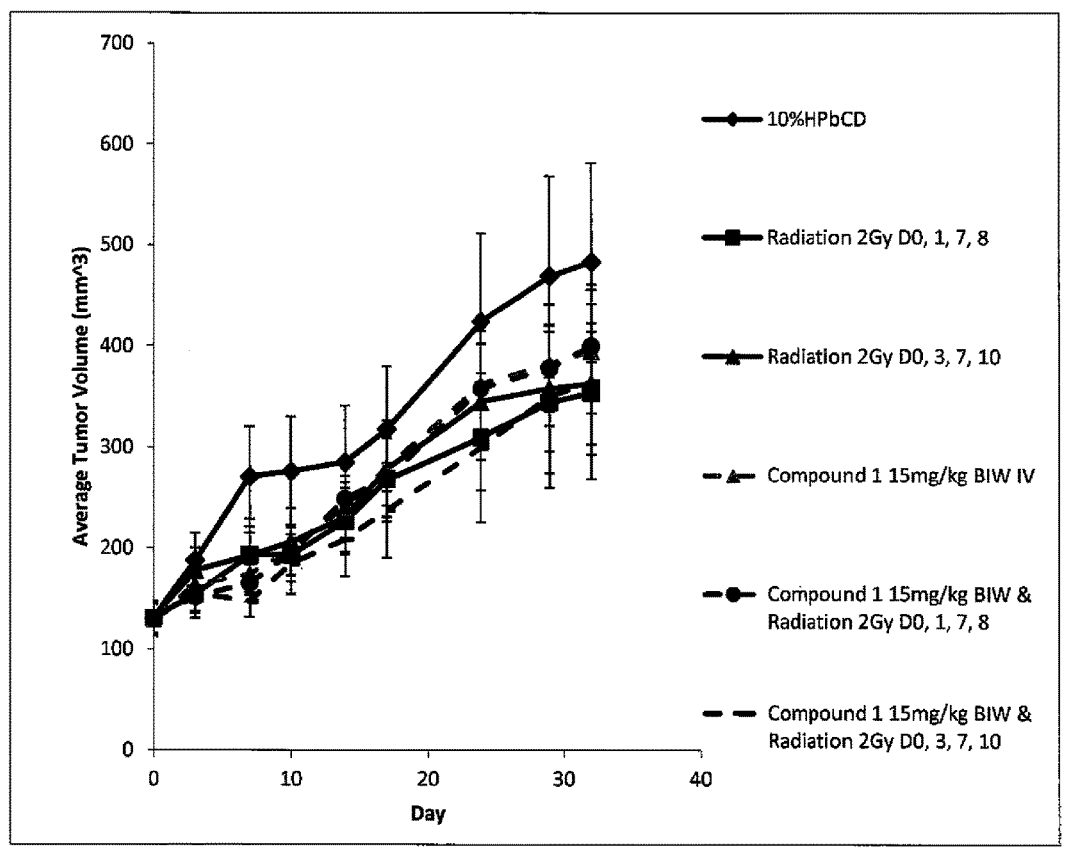

Figure 5b: The anti-tumor activity of Compound 1 at 6.25 mg/kg and Radiation in the HN-13-0007 xenograft model
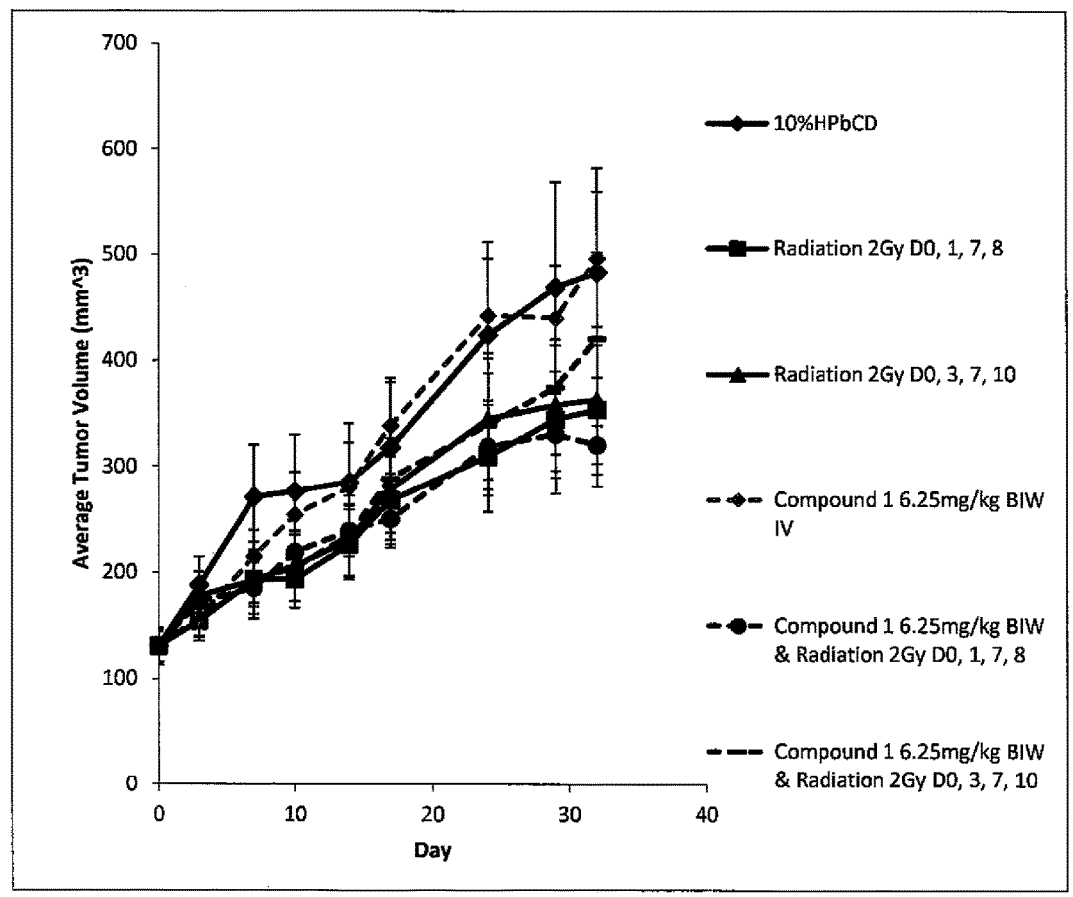

Figure 6: Percent Survival of HCT-116 Colonies Following Treatment Initiation with Compound 1 and Radiation
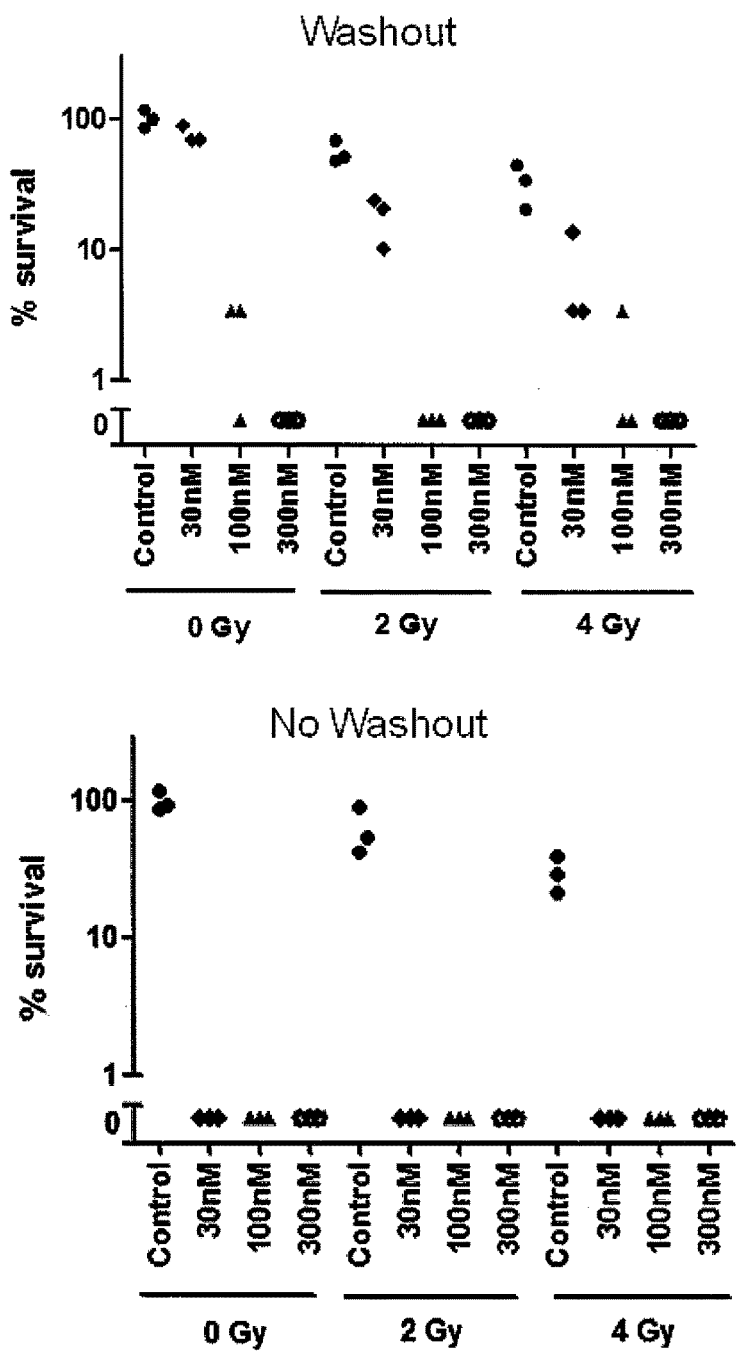

ADMINISTRATION OF UBIQUITIN-ACTIVATING ENZYME INHIBITOR AND RADIATION

FIELD

This present disclosure relates to oncology and to methods for the treatment of cancer. In particular, the present disclosure provides methods for treatment of various cancers by administering a ubiquitin-activating enzyme (UAE) inhibitor in combination with radiation.

BACKGROUND

Cancer is the second most common cause of death in the U.S. and accounts for one of every eight deaths globally (American Cancer Society, Cancer Facts and Figures, 2014). The American Cancer Society expects that in 2014 at least 1,665,540 new cancer cases will be diagnosed in the US and 585,720 Americans are expected to die of cancer, almost 1,600 people per day. Currently available paradigms for treating solid tumors may include systemic treatment such as chemotherapy, hormonal therapy, use of targeted agents and biological agents, either as single agents or in combination. These treatments can be delivered in combination with localized treatments such as surgery or radiotherapy. These anti-cancer paradigms can be use in the curative setting as adjuvant or neo-adjuvant treatments or in the metastatic setting as palliative case for prolonged survival and to help manage symptoms and side-effects. In hematological cancers, stem cell transplants may also be an option in certain cancers as well as chemotherapy and/or radiation. Although medical advances have improved cancer survival rates, there remains a continuing need for new and more effective treatments.

Ubiquitin is a small 76-amino acid protein that is the founding member of a family of posttranslational modifiers known as the ubiquitin-like proteins (Ubls). Ubls play key roles in controlling many biological processes including cell division, cell signaling and the immune response. There are 8 known human Ubl activating enzymes (known as E1s) (Schulman, B. A., and J. W. Harper, 2009, Ubiquitin-like protein activation by E1 enzymes: the apex for downstream signalling pathways, *Nat Rev Mol Cell Biol* 10:319-331). Ubiquitin and other Ubls are activated by a specific E1 enzyme which catalyzes the formation of an acyl-adenylate intermediate with the C-terminal glycine of the Ubl. The activated Ubl molecule is then transferred to the catalytic cysteine residue within the E1 enzyme through formation of a thioester bond intermediate. The E1-Ubl intermediate and an E2 enzyme interact, resulting in a thioester exchange wherein the Ubl is transferred from the E1 to active site cysteine on the E2. The Ubl is then conjugated, i.e. transferred, to the target protein, either directly or in conjunction with an E3 ligase enzyme, through isopeptide bond formation with the amino group of a lysine side chain in the target protein. Eukaryotic cells possess ~35 ubiquitin E2 enzymes and >500 ubiquitin E3 enzymes. The E3 enzymes are the specificity factors of the ubiquitin pathway which mediate the selective targeting of specific cellular substrate proteins (Deshaies, R. J., and C. A. Joazeiro, 2009, RING domain E3 ubiquitin ligases, *Annu Rev Biochem* 78:399-434; Lipkowitz, S., and A. M. Weissman, 2011, RINGs of good and evil: RING finger ubiquitin ligases at the crossroads of tumour suppression and oncogenesis, *Nat Rev Cancer* 11:629-643; Rotin, D., and S. Kumar, 2009, Physiological functions of the HECT family of ubiquitin ligases, *Nat Rev Mol Cell Biol* 10:398-409).

Two E1 enzymes have been identified for ubiquitin, UAE (ubiquitin-activating enzyme) and UBA6 (Jin, J., et al., 2007, Dual E1 activation systems for ubiquitin differentially regulate E2 enzyme charging, *Nature* 447:1135-1138). UAE is the E1 responsible for the majority (>99%) of ubiquitin flux within the cell. UAE is capable of charging each of the approximately ~35 E2 enzymes with the exception of Use1, which is the only E2 known to exclusively work with UBA6 (Jin et al., 2007). Inhibition of UAE is sufficient to dramatically impair the great majority of ubiquitin-dependent cellular processes (Ciechanover, A., et al., 1984, Ubiquitin dependence of selective protein degradation demonstrated in the mammalian cell cycle mutant ts85, *Cell* 37:57-66; Finley, D., A. et al., 1984, Thermolability of ubiquitin-activating enzyme from the mammalian cell cycle mutant ts85, *Cell* 37:43-55).

The cellular signals generated by ubiquitin are diverse. Ubiquitin can be attached to substrates as a single entity or as polyubiquitin polymers generated through isopeptide linkages between the C-terminus of one ubiquitin and one of the many lysines on a second ubiquitin. These varied modifications are translated into a variety of cellular signals. For example, conjugation of a lysine 48-linked polyubiquitin chain to a substrate protein is predominantly associated with targeting the protein for removal by the 26S proteasome. A single ubiquitin modification, or monoubiquination, typically affects protein localization and/or function. For example, monoubiquitination modulates the following: 1) the function of Histones 2a and 2b (Chandrasekharan, M. B., et al., 2010, Histone H2B ubiquitination and beyond: Regulation of nucleosome stability, chromatin dynamics and the trans-histone H3 methylation, *Epigenetics* 5:460-468), 2) controls the nucleo-cytoplasmic shuttling of PTEN (Trotman, L. C., et al., 2007, 3) ubiquitination regulates PTEN nuclear import and tumor suppression, *Cell* 128:141-156), 4) drives localization of the FANCD2 protein to sites of DNA damage (Gregory, R. C., et al., 2003, Regulation of the Fanconi anemia pathway by monoubiquitination, *Semin Cancer Biol* 13:77-82) and 5) promotes the internalization and endosomal/lysosomal turnover of some cell surface receptors, like EGFR (Mosesson, Y., and Y. Yarden, 2006, Monoubiquitylation: a recurrent theme in membrane protein transport. *Isr Med Assoc J* 8:233-237). Other forms of polyubiquitination chains occur on lysine positions 11, 29 and 63, impacting various cellular roles including cell cycle, DNA repair and autophagy (Behrends, C., and J. W. Harper, 2011, Constructing and decoding unconventional ubiquitin chains, *Nat Struct Mol Biol* 18:520-528; Bennett, E. J., and J. W. Harper, 2008, DNA damage: ubiquitin marks the spot, *Nat Struct Mol Biol* 15:20-22; Komander, D., 2009, The emerging complexity of protein ubiquitination, *Biochem Soc Trans* 37:937-953).

UAE-initiated ubiquitin conjugation plays an important role in protein homeostasis, cell surface receptor trafficking, transcription factor turnover and cell cycle progression. Many of these processes are important for cancer cell survival and it is believed that tumor cells may have increased sensitivity to UAE inhibition as a result of their rapid growth rate, increased metabolic demands and oncogene fueled protein stress. Preclinical studies with PYZD-4409, a UAE inhibitor, demonstrated this compound induced cell death in both leukemia and myeloma cell lines and induced anti-tumor activity in a mouse acute myeloid leukemia (AML model). (Xu, W. G., et al., 2010, The ubiquitin-activating enzyme E1 as a therapeutic target for the treatment of leukemia and multiple myeloma, *Blood,* 115:2251-59). Thus, UAE represents a protein homeostasis target opportunity for the treatment of cancer.

New combinations of therapeutic agents that provide a beneficial effect in the treatment of cancers are desirable in order to prolong patient's lives while maintaining a high quality of life. Furthermore, new combination therapies may provide an increased benefit as compared to each single agents used individually. This is especially true in the case where cancers may be resistant or refractory to currently available therapeutic regimens.

SUMMARY

In one aspect, the present disclosure relates to methods of treating cancer comprising administering an UAE inhibitor and radiation in combination to a subject in need of such treatment.

In one aspect, the present disclosure relates to methods of treating cancer comprising administering ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof and radiation in combination to a patient in need of such treatment.

In some embodiments, the cancer is a solid tumor.

In some embodiments, the cancer is breast cancer, colorectal cancer, ovarian cancer, lung cancer, prostate cancer, head and neck cancer, gastric cancer, esophageal cancer, or gastro-esophageal junction cancer.

In some embodiments, the cancer is breast cancer, colorectal cancer, ovarian cancer, lung cancer, prostate cancer, or head and neck cancer.

In some embodiments, the cancer is gastric cancer, esophageal cancer, or gastro-esophageal junction cancer.

In some embodiments, the cancer is a hematological cancer.

In some embodiments, the cancer is multiple myeloma, or non-Hodgkin's lymphoma.

In some embodiments, the radiation is particle radiation.

In some embodiments, the radiation is administered by external beam radiation.

In some embodiments, ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered on each of days 1 and 4 of each week repeated for 2 to 8 weeks.

In some embodiments, ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered on day 1 of each week repeated for 2 to 8 weeks.

In some embodiments, R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered on each of days 1-5 of each week repeated for 2 to 8 weeks.

In some embodiments, the radiation is administered on each of days 1-5 of each week repeated for 2 to 8 weeks.

In some embodiments, the radiation is administered on any two of days 1-5 of each week repeated for 5 to 8 weeks.

In some embodiments, ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered at a dose of about 4 mg to about 65 mg.

In some embodiments, ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered at a dose of about 15 mg to about 55 mg.

In some embodiments, ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered at a dose of about 18 mg to about 43 mg.

In some embodiments, the total dose of radiation administered is about 20 Gy to about 80 Gy.

In some embodiments, ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered on each of days 1 and 4 of each week repeated for 6 to 8 weeks and the radiation is administered on each of days 1-5 of each week repeated for 6 to 8 weeks.

In some embodiments, ((1R,2R,3S,4R)-2,3-dihydroxy-4-(2-(3-(trifluoromethylthio)phenyl)pyrazolo pyrimidin-7-ylamino)cyclopentyl)methyl sulfamate (Compound 1) or a pharmaceutically acceptable salt thereof is administered on day 1 each week repeated for 6 to 8 weeks and the radiation is administered on each of days 1-5 of each week repeated for 6 to 8 weeks.

In some embodiments, ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered on each of days 1-5 of each week repeated for 6 to 8 weeks and the radiation is administered on each of days 1-5 of each week repeated for 6 to 8 weeks.

In some embodiments, ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is not administered for any one or two week(s) of the 6-to-8-week period.

In some embodiments, the radiation is not administered for any one or two week(s) of the 6-to-8-week period.

In one aspect, the present disclosure relates to a medicament for use in treating cancer in a subject in need of such treatment, wherein the medicament comprises an UAE inhibitor and radiation.

BRIEF DESCRIPTION OF THE FIGURES

FIGS. 1a and 1b each shows a plot of tumor volume as a function of time in a HN-13-0014 xenograft model following administration of Compound 1 and radiation to mice.

FIGS. 2a, 2b, and 2c each shows a plot of tumor volume as a function of time in a LU-01-0030 xenograft model following administration of Compound 1 and radiation to mice.

FIGS. 3a and 3b each shows a plot of tumor volume as a function of time in a LU-01-0266 xenograft model following administration of Compound 1 and radiation to mice.

FIGS. 4a and 4b each shows a plot of tumor volume as a function of time in a ST-02-0004 xenograft model following administration of Compound 1 and radiation to mice.

FIGS. 5a and 5b each shows a plot of tumor volume as a function of time in a HN-13-0007 xenograft model following administration of Compound 1 and radiation to mice.

FIG. 6 shows percent survival of HCT-116 colonies following treatment initiation with Compound 1 and radiation.

DESCRIPTION

Definitions and Abbreviations

AUC area under the plasma concentration versus time curve
BSA body surface area
CR complete response
MTD maximum tolerated dose
UAE Ubiquitin-activating enzyme
PR partial response
BIW twice weekly
QD once daily
NSCLC non-small cell lung cancer
SCLC small cell lung cancer As used herein, the term "cancer" refers to a cellular disorder characterized by uncontrolled or dysregulated cell proliferation, decreased cellular differentiation, inappropriate ability to invade surrounding tissue, and/or ability to establish new growth at ectopic sites. The term "cancer" includes solid tumors and hematological tumors. The term "cancer" encompasses diseases of skin, tissues, organs, bone, cartilage, blood, and vessels. The term "cancer" further encompasses primary and metastatic cancers.

As used herein, "clinically effective amount" means an amount of a therapeutic substance that is sufficient upon appropriate administration to a patient (a) to cause a detectable decrease in the severity of the disorder or disease state being treated; (b) to ameliorate or alleviate the patient's symptoms of the disease or disorder; or (c) to slow, or prevent advancement of, or otherwise stabilize or prolong stabilization of, the disorder or disease state being treated (e.g., prevent additional tumor growth of a cancer).

When more than one therapeutic substance is being administered, the "clinically effective total amount" means that the sum of the individual amounts of each therapeutic substance meets the definition of "clinically effective amount" even if the individual amounts of any number of the individual therapeutic substances would not. For example, if 10 mg of A were not a clinically effective amount, and 20 mg of B were not a clinically effective amount, but the administration of 10 mg A+20 mg B resulted in at least one of the results enumerated for the definition of "clinically effective amount", then the sum of 10 mg A+20 mg B would be considered a "clinically effective total amount".

In any form or composition, the administered dose(s) or the clinically effective (total) amount can be expressed as amount(s) of therapeutic substance(s) per patient as either based on (i) BSA, e.g., as mg/m$^2$, or (ii) amount e.g. as mg.

As used herein, "patient" means a human being diagnosed with, exhibiting symptoms of or otherwise believed to be afflicted with a disease, disorder or condition.

As used herein, "body surface area" (BSA) is calculated using a standard nomogram, e.g., $$BSA(m^2) = \sqrt{\frac{Ht(cm) \times Wt(kg)}{3600}} \text{ or } BSA = \sqrt{\frac{Ht(in) \times Wt(lb)}{3131}}$$

As used herein the term "radiation" means ionizing radiation as used for cancer treatment.

As used herein, the illustrative terms "include", "such as", "for example" and the like (and variations thereof, e.g.,"includes" and "including", "examples"), unless otherwise specified, are intended to be non-limiting. That is, unless explicitly stated otherwise, such terms are intended to imply "but not limited to", e.g., "including" means including but not limited to.

Unless otherwise stated, structures depicted herein are meant to include chemical entities which differ only in the presence of one or more isotopically enriched atoms. For example, chemical entities having the present structure except for the replacement of a hydrogen atom by a deuterium or tritium, or the replacement of a carbon atom by a $^{13}$C- or $^{14}$C-enriched carbon are within the scope of the invention.

Unless stereochemical configuration is denoted, structures depicted herein are meant to include all stereochemical forms of the structure, i.e., the R and S configurations for each asymmetric center. Therefore, unless otherwise indicated, single stereochemical isomers as well as enantiomeric, racemic and diastereomeric mixtures of the present chemical entities are within the scope of the invention. When a stereochemical configuration is denoted for a compound, the diastereoisomeric or enantiomeric excess of the compound is at least 99.0%, 99.5%, 99.6%, 99.7%, 99.8% or 99.9%.

DETAILED DESCRIPTION

In one aspect, the present disclosure relates to a method of treating cancer in a patient by administering to a patient a combination of an UAE inhibitor or pharmaceutically acceptable salt thereof and radiation.

UAE inhibitors are disclosed in patent application publications WO2013/123169 and US 2014/0088096. In one embodiment, the UAE inhibitor is a compound having the following structure (Compound 1):

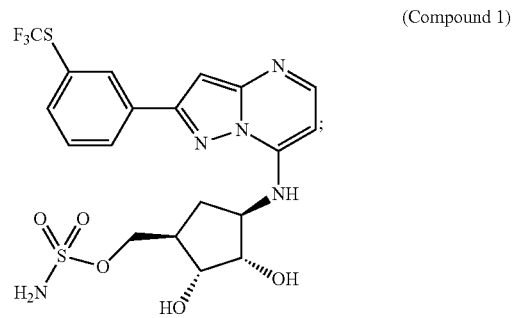

(Compound 1)

or a pharmaceutically acceptable salt thereof. The Compound 1 is named ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate.

In one aspect, the present disclosure relates to a method of treating cancer in a patient by administering to a patient a combination of Compound 1 or pharmaceutically acceptable salt thereof and radiation.

In some embodiments, the present disclosure relates to a method of treating cancer in a patient by administering to a patient a combination of Compound 1 and radiation.

In another aspect, the present disclosure relates to the use of Compound 1 or a pharmaceutically acceptable salt in combination with radiation for the treatment of cancer.

In another aspect, the present disclosure relates to the use of Compound 1 or a pharmaceutically acceptable salt in combination with radiation in the manufacture of a medicament for use in treating cancer.

In another aspect, the present disclosure relates to the use of Compound 1 or a pharmaceutically acceptable salt in the manufacture of a medicament for treating cancer, wherein Compound 1 or a pharmaceutically acceptable salt thereof is administered with radiation.

In some embodiments, the radiation is photon radiation (x-rays and gamma rays). In such embodiments, the photons are generated as a high energy photon beam from radioactive sources such as cobalt or a linear accelerator.

In some embodiments, the radiation is particle radiation (such as electrons, protons, neutrons, carbon ions, alpha particles, and beta particles. Particle radiation can be produced by linear accelerators. In some embodiments, the radiation is a electron beam. In some embodiments, the radiation is a proton beam. In some embodiments, the radiation is a neutron beam.

In some embodiments, the radiation is delivered by external beam radiation. In some embodiments, the external beam radiation is three-dimensional conformal radiation therapy (3D-CRT). In some embodiments, the external beam radiation is intensity modulated radiation therapy (IMRT). In some embodiments, the external beam radiation is image-guided radiation therapy (IGRT). In some embodiments, the external beam radiation is intensity modulated proton therapy (IMPT). In some embodiments, the external beam radiation is stereotactic radiosurgery (SRS). In some embodiments, the external beam therapy is fractionated stereotactic radiotherapy. In some embodiments, the external beam radiation is stereotactic body radiation therapy (SBRT). Examples of machines that deliver SBRT are Gamma Knife®, X-Knife®, CyberKnife®, and Clinac®.

In some embodiments the radiation is delivered by internal radiation therapy (brachytherapy). In such embodiments, the internal radiation therapy is interstitial radiation, for example, using small pellets, seeds, wires or tubes placed close to the cancer or tumor site. In such embodiments, the internal radiation therapy is intracavitary radiation, for example using a container of radioactive material that is placed in a body cavity.

In some embodiments, Compound 1 or a pharmaceutically acceptable salt is administered intravenously (IV). Pharmaceutical compositions suitable for IV administration of Compound 1 or a pharmaceutically acceptable are described in patent application publications WO2013/123169 and US 2013/0217682.

As used herein, the administration in "combination" of Compound 1 and radiation refers not only to simultaneous or sequential administration of the two agents, but also to the administration of both compounds during a single treatment cycle, as understood by one skilled in the art. In some embodiments, the radiation can be administered prior to administration of Compound 1. In some embodiments, the radiation can be administered at the same time as administration of Compound 1. In some embodiments, the radiation can be administered following administration of Compound 1.

In some embodiments, the cancer is a solid tumor. Non-limiting examples of solid tumors include pancreatic cancer; bladder cancer, including invasive bladder cancer; colorectal cancer; thyroid cancer; gastric cancer; breast cancer, including metastatic breast cancer; prostate cancer, including androgen-dependent and androgen-independent prostate cancer; renal cancer, including, e.g., metastatic renal cell carcinoma; liver cancer including e.g. hepatocellular cancer and intrahepatic bile duct; lung and bronchus cancer including non-small cell lung cancer (NSCLC), squamous lung cancer, bronchioloalveolar carcinoma (BAC), adenocarcinoma of the lung, and small cell lung cancer (SCLC); ovarian cancer including, e.g., progressive epithelial and primary peritoneal cancer; cervical cancer; uterine cancer including e.g. uterine corpus and uterine cervix; endometrial cancer; esophageal cancer; gastro-esophageal (GE) junction cancer; head and neck cancer, including, e.g., squamous cell carcinoma of the head and neck, nasopharyngeal cancer, oral cavity and pharynx; skin cancer, including, e.g., squamous cell skin cancer, basal cell skin cancer, Merkel cell carcinoma and melanoma; neuroendocrine cancer, including metastatic neuroendocrine tumors; brain cancer, including, e.g., glioma/glioblastoma, anaplastic oligodendroglioma, adult glioblastoma multiforme, and adult anaplastic astrocytoma; neuroendocrine cancer, including metastatic neuroendocrine tumors; bone cancer; penile cancer; anal cancer; and soft tissue sarcoma.

In some embodiments, the cancer is breast cancer, ovarian cancer, endometrial cancer, colorectal cancer, cervical cancer, lung cancer, gastric cancer, prostate cancer, testicular cancer, bladder cancer, esophageal cancer, melanoma, soft tissue sarcoma or head and neck cancer. In some embodiments, the cancer is breast cancer, colorectal cancer, ovarian cancer, lung cancer, prostate cancer, head and neck cancer, gastric cancer, esophageal cancer, or gastro-esophageal junction cancer. In some embodiments, the cancer is breast cancer, colorectal cancer, ovarian cancer, lung cancer, prostate cancer or head and neck cancer. In some embodiments, the cancer is breast cancer, colorectal cancer, ovarian cancer, or lung cancer. In some embodiments, the cancer is breast cancer, colorectal cancer, ovarian cancer, or non-small cell lung cancer. In some embodiments, the cancer is gastric cancer, esophageal cancer, or gastro-esophageal junction cancer.

In some embodiments, the cancer is lung cancer. Lung cancer includes different sub-types such as small cell lung cancer (SCLC); non-small cell lung cancer (NSCLC) including squamous NSCLC; bronchioloalveolar carcinoma (BAC); and adenocarcinoma. In some embodiments, the cancer is small cell lung cancer. In some embodiments, the cancer is non-small cell lung cancer.

In some embodiments, the cancer is breast cancer. Breast cancer includes different sub-types such as luminal A, luminal B, triple-negative (basal-like) and HER-2 type. In some embodiments, the cancer is triple-negative breast cancer.

In some embodiments, the cancer is ovarian cancer. Ovarian cancer includes different sub-types such as epithelial, germ-cell and sex-cord stromal. Primary peritoneal carcinoma is a related cancer that starts in the lining of the pelvis and abdomen. In some embodiments, the cancer is epithelial ovarian cancer.

In some embodiments, the cancer is prostate cancer. Prostate cancer includes androgen-dependent and androgen independent prostate cancer and adenocarcinomas.

In some embodiments, the cancer is colorectal cancer. Adenocarcinoma is the most common type of colorectal cancer. Other colorectal cancers may include gastrointestinal carcinoid tumors, gastrointestinal stromal tumors, and squamous cell carcinoma. In some embodiments, the cancer is rectal cancer.

In some embodiments, the cancer is head and neck cancer. Head and neck cancer are those that arise in the head and neck region and the cancer may be found in areas such as nasal cavities, sinuses, lips, mouth, salivary glands, pharynx or larynx. 90% of head and neck cancers are squamous cell carcinomas (SCCHN), which originate from the mucosal lining (epithelium) of these regions.

In some embodiments, the cancer is gastric cancer. Adenocarcinoma is the most common type of gastric cancer. Other gastric cancers may include gastrointestinal carcinoid tumors, gastrointestinal stromal tumors, and lymphomas.

In some embodiments, the cancer is esophageal cancer. The most common types of esophageal cancer are squamous cell carcinoma and adenocarcinoma. Gastro-esophageal cancer is a related cancer that develops at the point where the esophagus joins the stomach.

In some embodiments, the cancer is a hematological cancer. Non-limiting examples of hematologic malignancies include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma including diffuse large B-cell lymphoma (DLBCL); T-cell lymphoma; multiple myeloma (MM); amyloidosis; Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes, including polycythemia vera, essential thrombocythemia, and primary or idiopathic myelofibrosis.

In some embodiments, the cancer is acute myeloid leukemia, myelodysplastic syndromes, multiple myeloma, or non-Hodgkin's lymphoma. In some embodiments, the cancer is multiple myeloma or non-Hodgkin's lymphoma.

In some embodiments, Compound 1 or a pharmaceutically acceptable salt thereof is administered on a twice-weekly schedule repeated for 2 to 8 weeks. In some embodiments, Compound 1 or a pharmaceutically acceptable salt thereof is administered on each of days 1 and 4 of each week repeated for 2 to 8 weeks. In some embodiments, Compound 1 or a pharmaceutically acceptable salt thereof is administered on each of days 1 and 4 of each week repeated for 6 to 8 weeks. In some embodiments, Compound 1 or a pharmaceutically acceptable salt thereof is administered on each of days 1 and 4 of each week repeated for 2 weeks. In some embodiments, Compound 1 or a pharmaceutically acceptable salt thereof is administered on each of days 1 and 4 of each week repeated for 3 weeks. In some embodiments, Compound 1 or a pharmaceutically acceptable salt thereof is administered on each of days 1 and 4 of each week repeated for 4 weeks. In some embodiments, Compound 1 or a pharmaceutically acceptable salt thereof is administered on each of days 1 and 4 of each week repeated for 5 weeks. In some embodiments, Compound 1 or a pharmaceutically acceptable salt thereof is administered on each of days 1 and 4 of each week repeated for 6 weeks. In some embodiments, Compound 1 or a pharmaceutically acceptable salt thereof is administered on each of days 1 and 4 of each week repeated for 7 weeks. In some embodiments, Compound 1 or a pharmaceutically acceptable salt thereof is administered on each of days 1 and 4 of each week repeated for 8 weeks.

In some embodiments, Compound 1 or a pharmaceutically acceptable salt thereof is administered on a once-weekly schedule repeated for 2 to 8 weeks. In some embodiments, Compound 1 or a pharmaceutically acceptable salt thereof is administered on day 1 of each week repeated for 2 to 8 weeks. In some embodiments, Compound 1 or a pharmaceutically acceptable salt thereof is administered on day 1 of each week repeated for 6 to 8 weeks. In some embodiments, Compound 1 or a pharmaceutically acceptable salt thereof is administered on day 1 of each week repeated for 2 weeks. In some embodiments, Compound 1 or a pharmaceutically acceptable salt thereof is administered on day 1 of each week repeated for 3 weeks. In some embodiments, Compound 1 or a pharmaceutically acceptable salt thereof is administered on day 1 of each week repeated for 4 weeks. In some embodiments, Compound 1 or a pharmaceutically acceptable salt thereof is administered on day 1 of each week repeated for 5 weeks. In some embodiments, Compound 1 or a pharmaceutically acceptable salt thereof is administered on day 1 of each week repeated for 6 weeks. In some embodiments, Compound 1 or a pharmaceutically acceptable salt thereof is administered on day 1 of each week repeated for 7 weeks. In some embodiments, Compound 1 or a pharmaceutically acceptable salt thereof is administered on day 1 of each week repeated for 8 weeks.

In some embodiments, Compound 1 or a pharmaceutically acceptable salt thereof is administered on each of days 1-5 of each week repeated for 2 to 8 weeks. In some embodiments, Compound 1 or a pharmaceutically acceptable salt thereof is administered on each of days 1-5 of each week repeated for 6 to 8 weeks. In some embodiments, Compound 1 or a pharmaceutically acceptable salt thereof is administered on each of days 1-5 of each week repeated for 2 weeks. In some embodiments, Compound 1 or a pharmaceutically acceptable salt thereof is administered on each of days 1-5 of each week repeated for 3 weeks. In some embodiments, Compound 1 or a pharmaceutically acceptable salt thereof is administered on each of days 1-5 of each week repeated for 4 weeks. In some embodiments, Compound 1 or a pharmaceutically acceptable salt thereof is administered on each of days 1-5 of each week repeated for 5 weeks. In some embodiments, Compound 1 or a pharmaceutically acceptable salt thereof is administered on each of days 1-5 of each week repeated for 6 weeks. In some embodiments, Compound 1 or a pharmaceutically acceptable salt thereof is administered on each of days 1-5 of each week repeated for 7 weeks. In some embodiments, Compound 1 or a pharmaceutically acceptable salt thereof is administered on each of days 1-5 of each week repeated for 8 weeks.

In some embodiments, the amount of Compound 1 or a pharmaceutically acceptable salt thereof that is administered on each day of dosing is about 4 mg to about 65 mg. In some embodiments, the amount of Compound 1 or a pharmaceutically acceptable salt thereof that is administered on each day of dosing is about 5 mg to about 65 mg. In some embodiments, the amount of Compound 1 or a pharmaceutically acceptable salt thereof that is administered on each day of dosing is about 15 mg to about 55 mg. In some embodiments, the amount of Compound 1 or a pharmaceutically acceptable salt thereof that is administered on each day of dosing is between about 18 mg to about 43 mg. In some embodiments, the amount of Compound 1 or a pharmaceutically acceptable salt thereof that is administered on each day of dosing is about 18 mg, about 24 mg, about 30 mg, about 36 mg, about 43 mg, about 51 mg, or about 61 mg. All dosing amounts refer to the amount of Compound 1 administered, and do not include the weight amount of any pharmaceutically acceptable salt.

In some embodiments, the radiation is administered on each of days 1-5 of each week repeated for 2 to 8 weeks. In some embodiments, the radiation is administered on each of days 1-5 of each week repeated for 6 to 8 weeks. In some embodiments, the radiation is administered on each of days 1-5 of each week repeated for 2 weeks. In some embodiments, the radiation is administered on each of days 1-5 of each week repeated for 3 weeks. In some embodiments, the radiation is administered on each of days 1-5 of each week repeated for 4 weeks. In some embodiments, the radiation is administered on each of days 1-5 of each week repeated for 5 weeks. In some embodiments, the radiation is administered on each of days 1-5 of each week repeated for 6 weeks. In some embodiments, the radiation is administered on each of days 1-5 of each week repeated for 7 weeks. In some embodiments, the radiation is administered on each of days 1-5 of each week repeated for 8 weeks.

In some embodiments, the radiation is administered on any two of days 1-5 of each week repeated for 5 to 8 weeks. In some embodiments, the radiation is administered on any two of days 1-5 of each week repeated for 6 to 8 weeks. In some embodiments, the radiation is administered on any two of days 1-5 of each week repeated for 5 weeks. In some embodiments, the radiation is administered on any two of days 1-5 of each week repeated for 6 weeks. In some embodiments, the radiation is administered on any two of days 1-5 of each week repeated for 7 weeks. In some embodiments, the radiation is administered on any two of days 1-5 of each week repeated for 8 weeks.

The amount of radiation is measured in grays (Gy). In some embodiments, the total amount of radiation is about 20 Gy to about 80 Gy. In some embodiments, the total amount of radiation is about 20 Gy to about 40 Gy. In some embodiments, the total amount of radiation is about 40 to about 60 Gy. In some embodiments, the total amount of radiation is about 40 to about 80 Gy. Radiation doses are typically fractionated. In some embodiments, the radiation is administered at a dose of about 1.8 Gy to about 2 Gy per day. In some embodiments, the radiation is administered at a dose of about 2.67 Gy to about 2.75 Gy per day. In some embodiments, one dose is given per day. In some embodiments, the radiation may be given more than once per day (hyperfractionated radiation therapy). In some embodiments, two doses are given per day. In some embodiments, two doses are given per day with a minimum of 6 hours between the two doses. In some embodiments, three doses are given per day.

In some embodiments, Compound 1 or a pharmaceutically acceptable salt thereof is administered on each of days 1 and 4 of each week repeated for 6 to 8 weeks and radiation is administered on each of days 1-5 of each week repeated for 6 to 8 weeks. In some embodiments, Compound 1 or a pharmaceutically acceptable salt thereof is administered on each of days 1 and 4 of each week repeated for 6 weeks and radiation is administered on each of days 1-5 of each week repeated for 6 weeks. In some embodiments, Compound 1 or a pharmaceutically acceptable salt thereof is administered on each of days 1 and 4 of each week repeated for 7 weeks and radiation is administered on each of days 1-5 of each week repeated for 7 weeks. In some embodiments, Compound 1 or a pharmaceutically acceptable salt thereof is administered on each of days 1 and 4 of each week repeated for 8 weeks and radiation is administered on each of days 1-5 of each week repeated for 8 weeks. In some embodiments, Compound 1 or a pharmaceutically acceptable salt thereof is not administered for any one or two week(s) of the 6-to-8-week period. In some embodiments, radiation is not administered for any one or two week(s) of the 6-to-8-week period.

In some embodiments, Compound 1 or a pharmaceutically acceptable salt thereof is administered on day 1 of each week repeated for 6 to 8 weeks and radiation is administered on each of days 1-5 of each week repeated for 6 to 8 weeks. In some embodiments, Compound 1 or a pharmaceutically acceptable salt thereof is administered on day 1 of each week repeated for 6 weeks and radiation is administered on each of days 1-5 of each week repeated for 6 weeks. In some embodiments, Compound 1 or a pharmaceutically acceptable salt thereof is administered on day 1 of each week repeated for 7 weeks and radiation is administered on each of days 1-5 of each week repeated for 7 weeks. In some embodiments, Compound 1 or a pharmaceutically acceptable salt thereof is administered on day 1 of each week repeated for 8 weeks and radiation is administered on each of days 1-5 of each week repeated for 8 weeks. In some embodiments, Compound 1 or a pharmaceutically acceptable salt thereof is not administered for any one or two week(s) of the 6-to-8-week period. In some embodiments, radiation is not administered for any one or two week(s) of the 6-to-8-week period.

In some embodiments, Compound 1 or a pharmaceutically acceptable salt thereof is administered on each of days 1-5 of each week repeated for 6 to 8 weeks and radiation is administered on each of days 1-5 of each week repeated for 6 to 8 weeks. In some embodiments, Compound 1 or a pharmaceutically acceptable salt thereof is administered on each of days 1-5 of each week repeated for 6 weeks and radiation is administered on each of days 1-5 of each week repeated for 6 weeks. In some embodiments, Compound 1 or a pharmaceutically acceptable salt thereof is administered on each of days 1-5 of each week repeated for 7 weeks and radiation is administered on each of days 1-5 of each week repeated for 7 weeks. In some embodiments, Compound 1 or a pharmaceutically acceptable salt thereof is administered on each of days 1-5 of each week repeated for 8 weeks and radiation is administered on each of days 1-5 of each week repeated for 8 weeks. In some embodiments, Compound 1 or a pharmaceutically acceptable salt thereof is not administered for any one or two week(s) of the 6-to-8-week period. In some embodiments, radiation is not administered for any one or two week(s) of the 6-to-8-week period.

Therapeutic Substance; Pharmaceutical Compositions.

Any of therapeutic agents described herein can be in the form of a pharmaceutically acceptable salt. In some embodiments, such salts are derived from inorganic or organic acids or bases. For reviews of suitable salts, see, e.g., Berge et al., *J. Pharm. Sci.*, 1977, 66, 1-19 and *Remington: The Science and Practice of Pharmacy*, 20th Ed., A. Gennaro (ed.), Lippincott Williams & Wilkins (2000).

Examples of suitable acid addition salts include acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Examples of suitable base addition salts include ammonium salts; alkali metal salts, such as sodium and potassium salts; alkaline earth metal salts, such as calcium and magnesium salts; salts with organic bases, such as dicyclohexylamine salts, N-methyl-D-glucamine; and salts with amino acids such as arginine, lysine, and the like.

For example, Berge lists the following FDA-approved commercially marketed salts: anions acetate, besylate (benzenesulfonate), benzoate, bicarbonate, bitartrate, bromide, calcium edetate (ethylenediaminetetraacetate), camsylate (camphorsulfonate), carbonate, chloride, citrate, dihydrochloride, edetate (ethylenediaminetetraacetate), edisylate (1,2-ethanedisulfonate), estolate (lauryl sulfate), esylate (ethanesulfonate), fumarate, gluceptate (glucoheptonate), gluconate, glutamate, glycollylarsanilate (glycollamidophenylarsonate), hexylresorcinate, hydrabamine (N,N'-di(dehydroabietyl)ethylenediamine), hydrobromide, hydrochloride, hydroxynaphthoate, iodide, isethionate (2-hydroxyethanesulfonate), lactate, lactobionate, malate, maleate, mandelate, mesylate (methanesulfonate), methylbromide, methylnitrate, methylsulfate, mucate, napsylate (2-naphthalenesulfonate), nitrate, pamoate (embonate), pantothenate, phosphate/diphosphate, polygalacturonate, salicylate, stearate, subacetate, succinate, sulfate, tannate, tartrate, teoclate (8-chlorotheophyllinate) and triethiodide; organic cations benzathine (N,N'-dibenzylethylenediamine), chloroprocaine, choline, diethanolamine, ethylenediamine, meglumine (N-methylglucamine) and procaine; and metallic cations aluminum, calcium, lithium, magnesium, potassium, sodium and zinc.

Berge additionally lists the following non-FDA-approved commercially marketed (outside the United States) salts: anions adipate, alginate, aminosalicylate, anhydromethylenecitrate, arecoline, aspartate, bisulfate, butylbromide, camphorate, digluconate, dihydrobromide, disuccinate, glycerophosphate, hemisulfate, hydrofluoride, hydroiodide, methylenebis(salicylate), napadisylate (1,5-naphthalenedisulfonate), oxalate, pectinate, persulfate, phenylethylbarbiturate, picrate, propionate, thiocyanate, tosylate and undecanoate; organic cations benethamine (N-benzylphenethylamine), clemizole (1-p-chlorobenzyl-2-pyrrolidine-1'-ylmethylbenzimidazole), diethylamine, piperazine and tromethamine (tris(hydroxymethyl)aminomethane); and metallic cations barium and bismuth.

As used herein, "pharmaceutically acceptable carrier" refers to a material that is compatible with a recipient subject (a human) and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions for use in the methods of the present disclosure can be manufactured by methods well known in the art such as conventional granulating, mixing, dissolving, encapsulating, lyophilizing, or emulsifying processes, among others. Compositions can be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations can contain stabilizers, pH modifiers, surfactants, solubilizing agents, bioavailability modifiers and combinations of these.

Pharmaceutically acceptable carriers that can be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

These pharmaceutical compositions are formulated for pharmaceutical administration to a human being. Such compositions can be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. In some embodiments, the compositions are administered orally, intravenously or subcutaneously. In some embodiments, the compositions are administered orally. In some embodiments, the compositions are administered intravenously. These formulations can be designed to be short-acting, fast-releasing, or long-acting. Furthermore, the compositions can be administered in a local rather than systemic means, such as administration (e.g., by injection) at a tumor site.

Pharmaceutical formulations can be prepared as liquid suspensions or solutions using a liquid, such as an oil, water, an alcohol, and combinations of these. Solubilizing agents such as cyclodextrins can be included. Pharmaceutically suitable surfactants, suspending agents, or emulsifying agents, can be added for oral or parenteral administration. Suspensions can include oils, such as peanut oil, sesame oil, cottonseed oil, corn oil and olive oil. Suspension preparations can also contain esters of fatty acids such as ethyl oleate, isopropyl myristate, fatty acid glycerides and acetylated fatty acid glycerides. Suspension formulations can include alcohols, such as ethanol, isopropyl alcohol, hexadecyl alcohol, glycerol and propylene glycol; ethers, such as poly(ethyleneglycol); petroleum hydrocarbons such as mineral oil and petrolatum; and water.

Sterile injectable forms of these pharmaceutical compositions can be aqueous or oleaginous suspensions. These suspensions may be formulated according to techniques known in the art using suitable dispersing or wetting agents and suspending agents. The sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, such as carboxymethyl cellulose or similar dispersing agents which are commonly used in the formulation of pharmaceutically acceptable dosage forms including, emulsions and suspensions. Other commonly used surfactants, such as sorbitan alkyl esters, such as Tweens or Spans, and other emulsifying agents or bioavailability enhancers which are commonly used in the manufacture of pharmaceutically acceptable solid, liquid, or other dosage forms can also be used for the purposes of formulation. Compounds can be formulated for parenteral administration by injection such as by bolus injection or continuous infusion. A unit dosage form for injection can be in ampoules or in multi-dose containers.

These pharmaceutical compositions can be orally administered in any orally acceptable dosage form including capsules, tablets, aqueous suspensions or solutions. When aqueous suspensions are required for oral use, the active ingredient is combined with emulsifying and suspending agents. If desired, certain sweetening, flavoring or coloring agents can also be added. For oral administration in a capsule form, useful diluents include lactose and dried cornstarch. In the case of tablets for oral use, carriers that are commonly used include lactose and corn starch. Lubricating agents, such as magnesium stearate, are also typically added. Coatings may be used for a variety of purposes, e.g., to mask taste, to affect the site of dissolution or absorption, or to prolong drug action. Coatings can be applied to a tablet or to granulated particles for use in a capsule.

Alternatively, these pharmaceutical compositions can be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

These pharmaceutical compositions can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches can also be used. For topical applications, the pharmaceutical compositions can be formulated in a suitable ointment containing the active component suspended or dissolved in one or more carriers. Carriers for topical administration of the compounds of the present disclosure include mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active component(s) suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutical compositions can be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions can be formulated in an ointment such as petrolatum.

The pharmaceutical compositions can also be administered by nasal aerosol or inhalation. Such compositions are prepared according to techniques well known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

The methods of the present disclosure are directed to treating diseases, disorders and conditions in which inhibition of UAE enzyme activity is detrimental to survival and/or expansion of diseased cells or tissue (e.g., cells are sensitive to UAE inhibition; inhibition of UAE activity disrupts disease mechanisms; reduction of UAE activity stabilizes protein which are inhibitors of disease mechanisms; reduction of UAE activity results in inhibition of proteins which are activators of disease mechanisms). The diseases, disorders and conditions are also intended to include those which require effective cullin and/or ubiquitination activity, which activity can be regulated by diminishing NAE enzyme activity.

In some embodiments, the methods of the present disclosure further comprise administering a anti-cancer agent. As used herein, the term "anticancer agent" refers to any agent that is administered to a subject with cancer for purposes of treating the cancer. The administration of the further anti-cancer agent includes administration concurrently or sequentially with the combinations of the present disclosure. Alternatively, the further anti-cancer agent can be combined into one composition with the combinations of the present disclosure which is administered to the patient.

Non-limiting examples of anti-cancer agents include DNA damaging chemotherapeutic agents such as topoisomerase I inhibitors (e.g., irinotecan, topotecan, camptothecin and analogs or metabolites thereof); topoisomerase II inhibitors (e.g., etoposide, and teniposide); anthracyclines (e.g. doxorubicin, daunorubicin and idarubicin) alkylating agents (e.g., melphalan, chlorambucil, busulfan, thiotepa, ifosfamide, carmustine, lomustine, semustine, streptozocin, decarbazine, methotrexate, pemetrexed, mitomycin C, and cyclophosphamide); DNA intercalators; DNA intercalators and free radical generators such as bleomycin; and nucleoside mimetics (e.g., 5-fluorouracil, capecitibine, fludarabine, cytarabine, mercaptopurine, thioguanine, pentostatin, and hydroxyurea). Chemotherapeutic agents that disrupt cell replication include: vincristine, vinblastin, and related analogs; thalidomide, lenalidomide, and related analogs (e.g., CC-5013 and CC-4047); protein tyrosine kinase inhibitors (e.g., imatinib mesylate, erlotonib, crortinib and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, panitumumab, rituximab, cetuximab, and bevacizumab); and other inhibitors of proteins or enzymes known to be upregulated, over-expressed or activated in cancers, the inhibition of which downregulates cell replication.

In order that this present disclosure be more fully understood, the following examples are set forth. These examples are illustrative only and are not intended to limit the scope of the present disclosure in any way.

EXAMPLES

Methods of Synthesis

In another aspect, the present disclosure provides a process for making Compound 1 or a pharmaceutically acceptable salt thereof. A process suitable for the large scale production of Compound 1 or a pharmaceutically acceptable salt is disclosed herein.

In some embodiments, the present disclosure provides a process for making Compound 1:

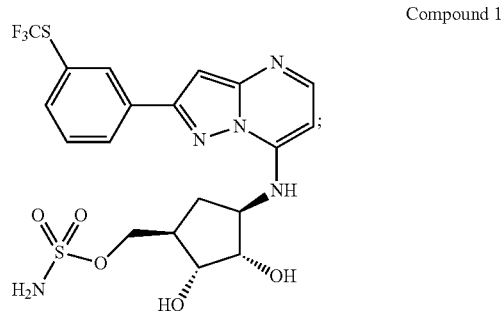

Compound 1 or pharmaceutically acceptable salt thereof, comprising the steps of:

a) contacting Compound 9 or a salt, solvate or hydrate thereof with 2,2-dimethyl-1,3-dioxane-4,6-dione (Meldrum's acid):

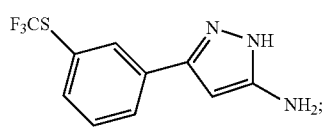
Compound 9 under coupling conditions to provide compound 8 or a salt, solvate or hydrate thereof:

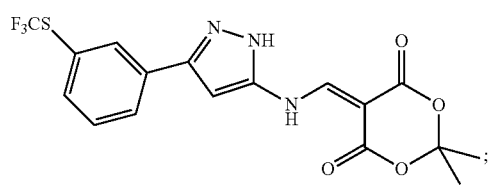
Compound 8 b) subjecting compound 8 or a salt, solvate or hydrate thereof to cyclization conditions to provide compound 7 or a salt, solvate or hydrate thereof

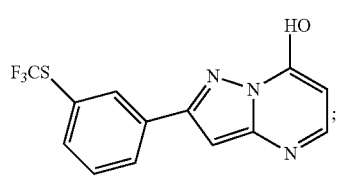
Compound 7 c) contacting Compound 7 or a salt, solvate or hydrate thereof with benzotriazole under chlorination/displacement conditions to provide Compound 5 or a salt, complex, solvate or hydrate thereof:

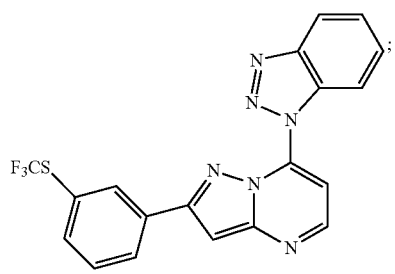
Compound 5 d) contacting Compound 5 or a salt, complex, solvate or hydrate thereof with Compound 6 or a salt, solvate or hydrate thereof:

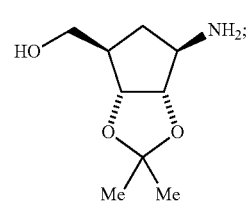
Compound 6 under displacement reaction conditions to provide Compound 3 or a salt, solvate or hydrate thereof

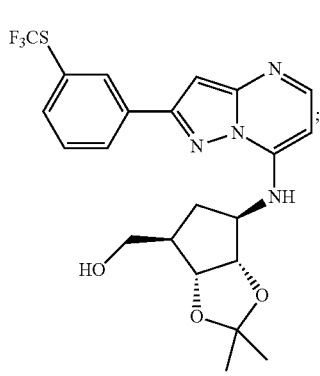
Compound 3 e) contacting Compound 3 or a salt, solvate or hydrate thereof with Compound 4

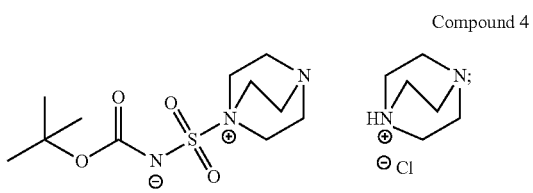 [SMILES: CC(C)(C)OC(=O)[N-]S(=O)(=O)[N+]12CCN(CC1)CC2 ; C1C[NH+]2CCN1CC2 ; [Cl-]]
Compound 4 under sulfamoylating reaction conditions to provide Compound 2 or a salt, solvate or hydrate thereof

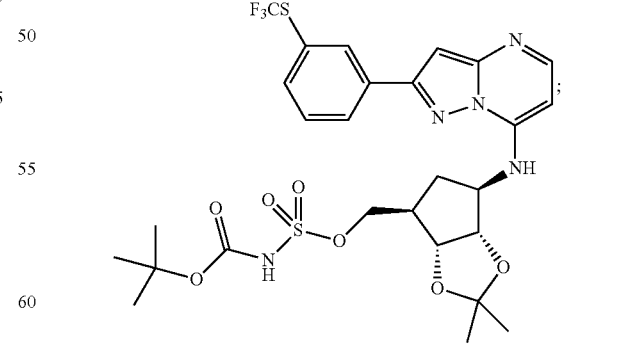
Compound 2 f) contacting Compound 2 or a salt, solvate or hydrate thereof with an acid under sulfamoylation conditions to provide Compound 1 or a pharmaceutically acceptable salt thereof

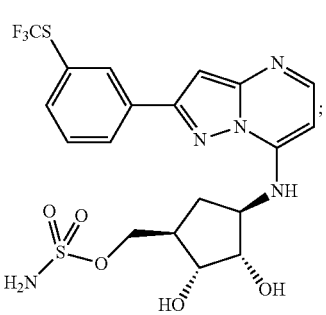

Compound 1

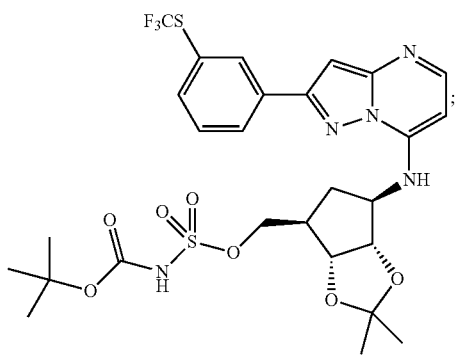

Compound 2 g) and optionally recrystallizing Compound 1 or a pharmaceutically acceptable salt under recrystallization conditions.

In some embodiments, the present disclosure provide a process for recrystallizing Compound 1 or a pharmaceutically acceptable salt thereof to provide Compound 1 or a pharmaceutically acceptable salt using recrystallization conditions. The recrystallizing may be done to remove impurities.

In some embodiments, Compound 1 or a pharmaceutical salt thereof is Compound 1 Form 1; a anhydrous crystalline form that is described in patent applications WO2013/123169 and US 2013/0217682. In some embodiments, Compound 1 or a pharmaceutical salt thereof is Compound 1 Form 2; a monohydrated crystalline form that is described in patent applications WO2013/123169 and US 2013/0217682.

In one embodiment, the recrystallization conditions of the disclosure comprise an aqueous solvent mixture. In some embodiments, the solvent is acetonitrile, ethyl acetate, dimethylformamide, dimethylacetamide, N-methylpyrrolidone or dimethylsulfoxide. In some embodiments, the solvent is acetonitrile. In some embodiments, the amount of water in the aqueous solvent mixture is about 5% to about 70%. In some embodiments, the amount of water in the aqueous solvent mixture is about 45% to about 65%.

In some embodiments, the present disclosure provides a process for making Compound 1:

under deprotection reaction conditions to provide Compound 1 or a pharmaceutically acceptable salt thereof.

In one embodiment, the deprotection reaction conditions of the disclosure comprise an aqueous acid. A variety of acids may be suitable for deprotecting the protecting groups in Compound 2. Non-limiting examples of suitable acids include phosphoric acid, sulfuric acid, trifluoracetic acid, acetic acid, and hydrochloric acid. In some embodiments, the acid is phosphoric acid. In some embodiments, the acid is sulfuric acid.

In one embodiment, the deprotection temperature is about 0° C. to about 25° C. In other embodiments, the deprotection temperature is about 0° C. to room temperature.

In one embodiment, the deprotection reaction conditions comprise a solvent. Non-limiting examples of suitable solvents include dimethylformamide, dimethylacetamide, N-methylpyrrolidone, acetonitrile, isopropanol, ethanol, methanol, dimethylsulfoxide, water, tetrahydrofuran, 2-methyltetrahydrofuran, dichloromethane or mixtures thereof. In some embodiments, the solvent is acetonitrile.

In some embodiments, the present disclosure provides a process for making Compound 2:

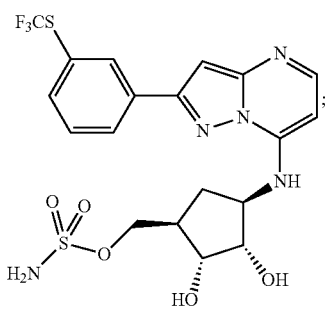

Compound 1

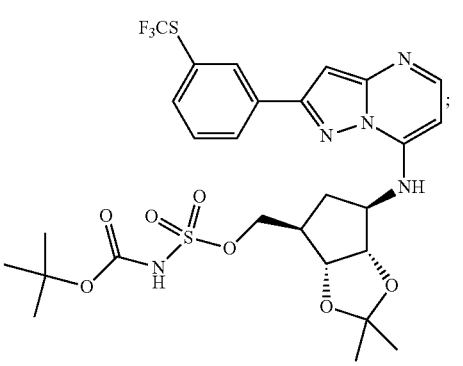

Compound 2 or pharmaceutically acceptable salt, solvate or hydrate thereof comprising contacting compound 2 or a pharmaceutically acceptable salt thereof with an acid:

or a salt, solvate or hydrate thereof comprising contacting Compound 3 or a salt, solvate or hydrate thereof with Compound 4:

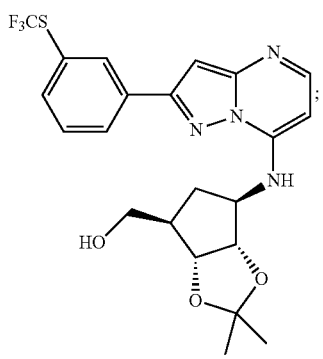

Compound 3

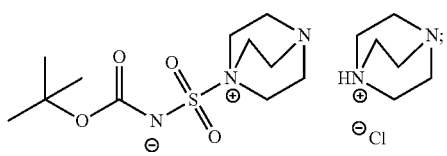

Compound 4 under sulfamoylating reaction conditions to provide Compound 2 or a pharmaceutically acceptable salt thereof.

In one embodiment, the sulfamoylating reaction conditions of the disclosure comprise a weak acid or a weak base. In some embodiments, the weak acid is pyridinium p-toluenesulfonate, tosic acid, citric acid, benzoic acid, camphorsulfonic acid, nosic acid or mesic acid. In some embodiments, the weak acid is pyridinium p-toluenesulfonate. In some embodiments, the weak base is pyridine, dimethylaminopyridine, tetramethylpyridine or 2,6-lutidine.

Compound 4 can be prepared by methods such as those described in Armitage, I. et al, *Org. Lett.;* 2012, 14, 2626-2629, and Armitage, I. et al, US Patent Appl. Publication 2009/0036678. In some embodiments, about 1 molar equivalents to about 5 molar equivalents of the Compound 4 (with respect to Compound 3) are used. In some embodiments, about 2.5 molar equivalents to about 3 molar equivalents of Compound 4 (with respect to Compound 3) are used.

In one embodiment, the sulfamoylating reaction conditions of the disclosure comprise a solvent. Non-limiting examples of suitable solvent include dimethylformamide, dimethylacetamide, N-methylpyrrolidone, acetonitrile, tetrahydrofuran, dimethylsulfoxide, toluene, 2-methyltetrahydrofuran or mixtures thereof. In some embodiments, the solvent is acetonitrile.

In some embodiments, the present disclosure provides a process for making Compound 3:

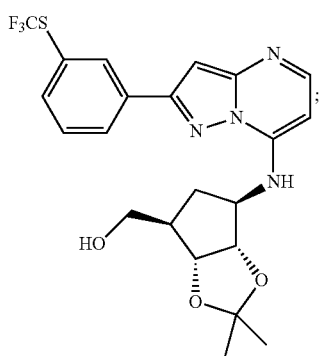

Compound 3 or a salt, solvate or hydrate thereof comprising contacting Compound 5 or a salt, complex, solvate or hydrate thereof with Compound 6 or a salt, solvate or hydrate thereof:

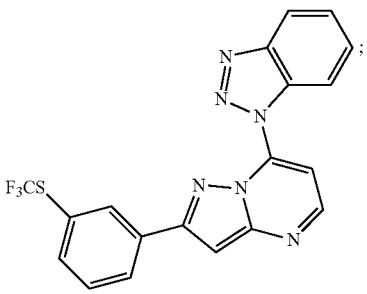

Compound 5

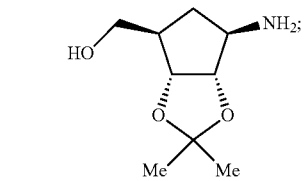

Compound 6 under displacement reaction conditions.

In one embodiment, the displacement reaction conditions of the disclosure comprise a neat base. Non-limiting examples of bases that can be use neat for the displacement reaction include triethylamine, diisopropylethylamine, triispropylamine, tributylamine, pyridine, and pyrrolidine. In some embodiments, the neat base is triethylamine.

In one embodiment, the displacement reaction conditions of the disclosure comprise a base and solvent. In some embodiments, the base is triethylamine, diisopropylethylamine, triispropylamine, tributylamine, pyridine, pyrrolidine, triethylenediamine (DABCO) and diazabicycloundecene (DBU). In some embodiments, the solvent is isopropanol, ethanol, acetonitrile, dimethylsulfoxide, tetrahydrofuran, 2-methyltetrahydrofuran, dimethylformamide, N-methylpyrrolidine and toluene. In some embodiments, the base and solvent are triethylamine and isopropanol.

In one embodiment, the displacement reaction conditions of the disclosure comprise an elevated temperature. In some embodiments, the elevated temperature is about 50° C. to about 110° C. In some embodiments, the elevated temperature is about 70° C. to about 90° C.

In one embodiment Compound 6 is the hydrochloride salt. Compound 6 can be prepared by methods known in the scientific literature [See for example: A) Saksena, A. K. *Tetrahedron Lett,* 1980, 21, 133-136. B) Hutchinson, E. J.; Taylor, B. F.; Blackburn, G. M. *J. Chem. Soc., Chem. Commun.* 1997, 1859-1860. C) Tokoro, Y. *Chem. Commun,* 1999, 807-809. D) Dominguez, B. M.; Cullis, P. M. *Tetrahedron Lett.,* 1999, 40, 5783-5786]. Compound 6 hydrochloride salt can be prepared in an analogous manner to that described in Armitage, I. et al, US Patent Appl. Publication 2009/0036678.

In another embodiment, the present disclosure provides Compound 5:

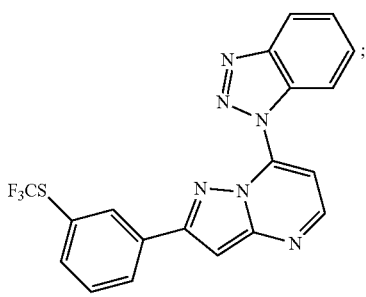

Compound 5 or a salt, solvate or hydrate thereof. In one embodiment, Compound 5 is a Compound 5-hydrochloride-tertiary amine complex. In some embodiments, the tertiary amine is triethylamine. In some embodiments the amount of hydrochloride-triethylamine present in the complex is about 0% to about 200% based on the amount of Compound 5 present in the complex. In some embodiments the amount of hydrochloride-triethylamine present in the complex is about 0% to about 130% based on the amount of Compound 5 present in the complex.

In some embodiments, the present disclosure provides a process for making Compound 5:

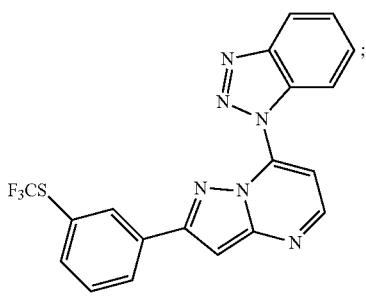

Compound 5 or a salt, complex, solvate or hydrate thereof comprising contacting Compound 7 or a salt, solvate or hydrate thereof with benzotriazole:

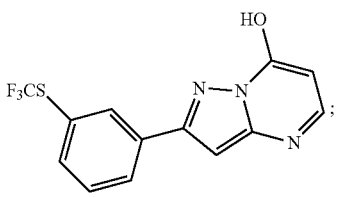

Compound 7 under chlorination/displacement conditions.

In one embodiment, the chlorination/displacement reaction conditions of the disclosure comprise a chlorinating reagent. In some embodiments, the chlorinating reagent is thionyl chloride or phosphoryl chloride. In some embodiments, the chlorinating reagent is phosphoryl chloride.

In one embodiment, the chlorination/displacement reaction conditions of the disclosure comprise a solvent. In some embodiments, the solvent is acetonitrile, tetrahydrofuran, toluene or dichloroethane. In some embodiments, the solvent is acetonitrile.

In one embodiment, the chlorination/displacement reaction conditions of the disclosure comprise a base. In some embodiments, the base is triethylamine, diisopropylethylamine, triisopropylamine, tributylamine, or tripropylamine. In some embodiments, the base is triethylamine.

In one embodiment, the chlorination/displacement reaction conditions of the disclosure comprise an elevated temperature. In some embodiments, the elevated temperature is about 50° C. to about 110° C. In some embodiments, the elevated temperature is about 70° C. to about 90° C.

In another embodiment, the present disclosure provides Compound 7:

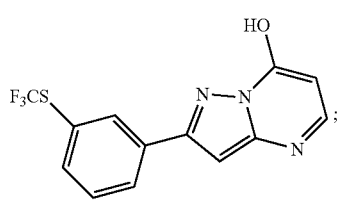

Compound 7 or a salt, solvate or hydrate thereof.

In some embodiments, the present disclosure provides a process for making Compound 7:

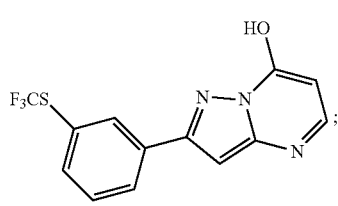

Compound 7 or a salt, solvate or hydrate thereof comprising subjecting Compound 8 or a salt, solvate or hydrate thereof:

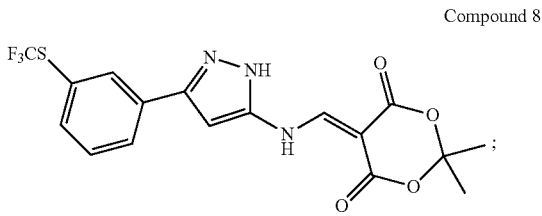

Compound 8 to cyclization conditions.

In one embodiment, the cyclization reaction conditions of the disclosure comprise a solvent. Suitable solvents include 1,2-dichlorobenzene, chlorobenzene, nitrobenzene, quinuclidine and N-methylpyrrolidone. In some embodiments, the solvent is heat transfer fluid which is a eutectic mixture of biphenyl and diphenyl oxide (DOWTHERM A). In some embodiments, the solvent is 1,2-dichlorobenzene.

In one embodiment, the cyclization reaction conditions of the disclosure comprise an elevated temperature. In some embodiments, the elevated temperature is about 140° C. to about 180° C. In some embodiments, the elevated temperature is about 145° C. to about 165° C.

In one embodiment, the cyclization reaction conditions of the disclosure provide a selective cyclization that prevents formation of the alternative regio-isomer (Compound 10):

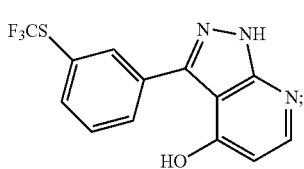

Compound 10

In another embodiment, the present disclosure provides Compound 8:

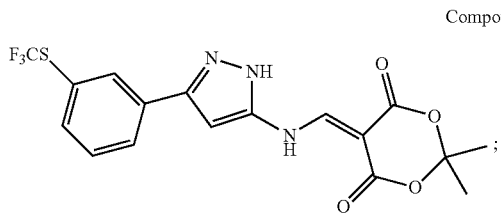

Compound 8 or a salt, solvate or hydrate thereof.

In some embodiments, the present disclosure provides a process for making Compound 8:

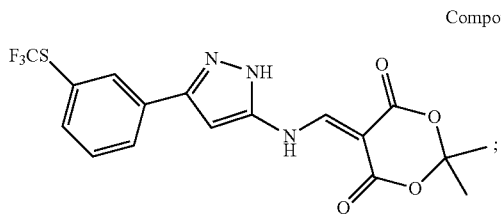

Compound 8 or a salt, solvate or hydrate thereof comprising contacting Compound 9 or a salt, solvate or hydrate thereof with 2,2-dimethyl-1,3-dioxane-4,6-dione (Meldrum's acid):

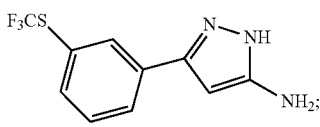

Compound 9 to coupling reaction conditions.

In one embodiment, the coupling reaction conditions of the disclosure comprise a solvent. Suitable solvents include isopropanol, acetonitrile, tetrahydrofuran, 2-methyltetrahydrofuran and dichloromethane.

In one embodiment, the coupling reaction conditions of the disclosure comprise an orthoester. In some embodiments, the orthoester is trimethylorthoformate or triethylorthoformate. In some embodiments, the orthoester is trimethylorthoformate. In one embodiment, the coupling reaction conditions of the disclosure comprise dimethylformamide dimethylacetal.

In one embodiment, the coupling temperature is about room temperature to about 25° C. In other embodiments, the coupling temperature is about 70° C. to about 90° C.

In another embodiment, the present disclosure provides Compound 9:

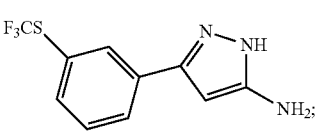

Compound 9 or a salt, solvate or hydrate thereof.

In order that this present disclosure be more fully understood, the following examples are set forth. These examples are illustrative only and are not intended to limit the scope of the present disclosure in any way.

EXAMPLES

Abbreviations h hour
min minutes
HPLC High-pressure liquid chromatography
UPLC Ultra-pressure liquid chromatography
NMR Nuclear Magnetic Resonance
THF tetrahydrofuran
General Analytical Methods Unless otherwise stated 1H NMR spectra were obtained using a Varian 300 MHz. Unless otherwise stated HPLC were obtained on Agilent 1100 Series and UPLC were obtained by Water Acuity Systems.

Example 1: Synthesis of 3-{3-[(trifluoromethyl)sulfanyl]phenyl}-1H-pyrazol-5-amine Step A: 3-((trifluoromethyl)thio)benzoate To dimethylcarbonate (68 mL) was added 3-((trifluoromethyl)thio)benzoic acid (100 g, Beta Pharma Scientific) and a catalytic amount of sulfuric acid (2.4 mL). The mixture was then heated to 90° C. for 5 h. The reaction was then cooled to room temperature and quenched with sodium bicarbonate (1.0 L). To the aqueous layer was with ethyl acetate (1.0 L). The phases were separated and this process was repeated with ethyl acetate (1.0 L). The organic layers were combined and concentrated with a rotovap to give a light orange oil. The methyl 3-((trifluoromethyl)thio)benzoate (105 g, 99%) was taken on crude to the next reaction. $^1$H NMR (300 MHz, CHLOROFORM-d) δ ppm 3.99 (s, 3H) 7.49-7.58 (m, 1H) 7.85 (d, J=7.62 Hz, 1H) 8.17 (dt, J=7.69, 1.43 Hz, 1H) 8.32-8.44 (m, 1H).

Step B: 3-oxo-3-(3-((trifluoromethyl)thio)phenyl)propanenitrile

Methyl 3-((trifluoromethyl)thio)benzoate (100.0 g) in tetrahydrofuran (1.0 L) was added acetonitrile (44.2 mL, 847 mmol) and 1M (in THF) potassium tert-butoxide (95.01 g). The reaction was complete in 10 min by HPLC analysis. The reaction was quenched with 1M HCl (1.0 L) and then extracted with three times with (1.0 L) of ethyl acetate. The organic layers with 3-oxo-3-(3-((trifluoromethyl)thio)phenyl)propanenitrile were then concentrated to dryness. This material (100.0 g, 96.3%) was taken on crude with further purification. $^1$H NMR (300 MHz, CHLOROFORM-d) δ ppm 4.12 (s, 2H) 7.51-7.75 (m, 1H) 7.89-8.01 (m, 1H) 8.01-8.10 (m, 1H) 8.20 (s, 1H)

Step C: 3-{3-[(trifluoromethyl)sulfanyl]phenyl}-1H-pyrazol-5-amine

To 3-oxo-3-{3-[(trifluoromethyl)sulfanyl]phenyl} propanenitrile (100.0 g,) in ethanol (1000.0 mL) was added hydrazine hydrate (59.52 mL). The reaction was heated to 100° C. for 1 h at which point HPLC analysis showed the reaction was complete. The reaction was concentrated to dryness on a rotovap to give a brown oil. The oil was taken up in ethyl acetate (1.0 L) and extracted with water (1.0 L). The phases were separated and the organic phase was concentrated. Upon concentration 3-{3-[(trifluoromethyl)sulfanyl]phenyl}-1H-pyrazol-5-amine was obtained (80.8 g; Yield=76.4%). $^1$H NMR (300 MHz, CHLOROFORM-d) δ ppm 5.95 (s, 1H) 6.73 (br s, 1H) 7.13-7.34 (m, 2H) 7.42-7.74 (m, 3H) 7.85 (s, 1H).

Example 2: ((1R,2R,3S,4R)-2,3-dihydroxy-4-((2-(3-((trifluoromethyl)thio)phenyl)pyrazolo[1,5-a]pyrimidin-7-yl)amino)cyclopentyl)methyl sulfamate

Step 1: (2,2-dimethyl-5-(((3-(3-((trifluoromethyl)thio)phenyl)-1H-pyrazol-5-yl)amino)methylene)-1,3-dioxane-4,6-dione)

To trimethoxy orthoformate (2.0 L), at 20° C. and under a blanket of nitrogen, was added 2,2-dimethyl-1,3-dioxane-4,6-dione (361.35 g). The resulting white suspension went clear within minutes and was heated to 85° C. over 15 minutes. The reaction was held at 85° C. for 120 minutes. While the reaction was heated and stirred another solution of 3-(3-((trifluoromethyl)thio)phenyl)-1H-pyrazol-5-amine (500.0 g) was made. To a 4 L RBF was added 3-(3-((trifluoromethyl)thio)phenyl)-1H-pyrazol-5-amine (500.0 g) and then trimethoxy orthoformate (1.4 L) added into this solid. This solution was mixed to dissolve the solids and resulted a dark brown solution. The solution of 3-(3-((trifluoromethyl)thio)phenyl)-1H-pyrazol-5-amine (~1.8 L in trimethoxy orthoformate) was added to the reactor over 30 minutes while maintaining the reaction temperature at 85° C. The reaction was then stirred for 20 minutes with white solids forming in the solution. After 20 minutes the reaction was sampled and the UPLC showed the complete conversion of 3-(3-((trifluoromethyl)thio)phenyl)-1H-pyrazol-5-amine to 2,2-dimethyl-5-(((3-(3-((trifluoromethyl)thio)phenyl)-1H-pyrazol-5-yl)amino)methylene)-1,3-dioxane-4,6-dione. The reaction was cooled to 20° C. over 20 minutes and maintained at that temperature for 20 additional minutes. At this point, a thick white slurry had formed and the reaction was filtered using a Nutche Filter over 15 minutes. The reactor was washed with 1 L of ethyl acetate and this solution was then mixed with the filter cake and removed by filtration. The cake was dried for ~40 minutes on the filter and then transferred to a vacuum oven and heated at 40° C. under full vacuum overnight (16 hours). The reaction was then analyzed by HPLC and NMR to give 2,2-dimethyl-5-(((3-(3-((trifluoromethyl)thio)phenyl)-1H-pyrazol-5-yl)amino)methylene)-1,3-dioxane-4,6-dione (635.3 g, 79%)$^1$H NMR (300 MHz, DMSO-d$_6$) δ ppm 1.68 (s, 6H) 7.05 (d, J=2.05 Hz, 1H) 7.64-7.77 (m, 2H) 7.77-8.03 (m, 1H) 8.12 (s, 1H) 8.72 (d, J=14.36 Hz, 1H) 11.35 (d, J=14.66 Hz, 1H) 13.47 (s, 1H).

Step 2: 2-(3-((trifluoromethyl)thio)phenyl)pyrazolo[1,5-a]pyrimidin-7-ol

A solution of 2,2-dimethyl-5-(((3-(3-((trifluoromethyl)thio)phenyl)-1H-pyrazol-5-yl)amino)methylene)-1,3-dioxane-4,6-dione (615.00 g) in 1,2-dichlorobenzene (6.3 L) was stirred at ambient temperature for 10 minutes. The solution was then heated to 150° C. over 75 minutes. The reaction was maintained at this temperature for 16 hours. An sample was taken after 16 hours and the UPLC analysis showed the complete conversion of 2,2-dimethyl-5-(((3-(3-((trifluoromethyl)thio)phenyl)-1H-pyrazol-5-yl)amino)methylene)-1,3-dioxane-4,6-dione to 2-(3-((trifluoromethyl)thio)phenyl)pyrazolo[1,5-a]pyrimidin-7-ol. The reaction was cooled to 20° C. over 130 minutes. At this point, a thick white slurry had formed and the reaction was filtered using a Nutche Filter over 15 minutes. The reactor was washed with 1.8 L of acetonitrile and this solution was then mixed with the filter cake and then the solvent was removed by filtration. The cake was dried for ~40 minutes on the filter and then transferred to a vacuum oven and heated at 40° C. under full vacuum overnight (16 hours). The reaction was then analyzed by HPLC and NMR to give 2-(3-((trifluoromethyl)thio)phenyl)pyrazolo[1,5-a]pyrimidin-7-ol (331.2 g, 72%) $^1$H NMR (300 MHz, METHANOL-d$_4$) δ ppm 6.55 (d, J=7.33 Hz, 1H) 7.59 (s, 1H) 8.40-8.52 (m, 1H) 8.53-8.64 (m, 1H) 8.69 (d, J=7.62 Hz, 1H) 9.01 (dt, J=7.77, 1.39 Hz, 1H) 9.12 (s, 1H) 13.34 (s, 1H).

Step 3: 1-(2-(3-((trifluoromethyl)thio)phenyl)pyrazolo[1,5-a]pyrimidin-7-yl)-1H-benzo[d][1,2,3]triazole:triethylamine:hydrochloride complex (1:1.25:1.25 moles:moles:moles)

To a solution of 2-(3-((trifluoromethyl)thio)phenyl)pyrazolo[1,5-a]pyrimidin-7-ol (30.00 g), benzotriazole (287.02 g) in acetonitrile (3000 mL) and triethylamine (403.00 mL) at 0° C., was added phosphoryl chloride (108 mL) slowly under a blanket of nitrogen, maintaining <10° C. The reaction was then warmed to 80° C. over 45 minutes and stirred for 240 minutes. HPLC indicated complete consumption of starting material. To the reaction mixture was added acetonitrile (3000 mL) while maintaining the temperature at 80° C. The reaction was then cooled to 20° C. over 80 minutes. The reaction was then stirred at ambient temperature for 14 hours. At this point, a thick slurry had formed and the reaction was filtered using a Nutche filter over 15 minutes. The reactor was washed twice with 900 mL of acetonitrile and this solution was then mixed with the filter cake and then the solvent was removed by filtration. The cake was dried for ~40 minutes on the filter and then transferred to a vacuum oven and heated at 40° C. under full vacuum overnight (16 h). The reaction was then analyzed by HPLC and NMR to give 1-(2-(3-((trifluoromethyl)thio)phenyl)pyrazolo[1,5-a]pyrimidin-7-yl)-1H-benzo[d][1,2,3]triazole:triethylamine:hydrochloride complex (1:1.25:1.25 moles:moles:moles) (438.1 g, 83%). $^1$H NMR (300 MHz, DMSO-d$_6$) δ ppm 1.19 (t, J=7.33 Hz, 12H) 3.07 (qd, J=7.28, 4.84 Hz, 8H) 7.60-7.78 (m, 6H) 7.80-7.87 (m, 1H) 8.15 (dt, J=7.99, 1.28 Hz, 1H) 8.24 (s, 1H) 8.33 (dt, J=8.14, 0.92 Hz, 1H) 8.85 (d, J=4.69 Hz, 1H).

Step 4: ((3aR,4R,6R,6aS)-2,2-dimethyl-6-((2-(3-((trifluoromethyl)thio)phenyl)pyrazolo[1,5-a]pyrimidin-7-yl)amino)tetrahydro-3aH-cyclopenta[d][1,3]dioxol-4-yl)methanol To the reactor was added 1-(2-(3-((trifluoromethyl)thio)phenyl)pyrazolo[1,5-a]pyrimidin-7-yl)-1H-benzo[d][1,2,3]triazole:triethylamine:hydrochloride complex (1:1.25:1.25 moles:moles:moles) (430.0 g) and ((3aR,4R,6R,6aS)-6-amino-2,2-dimethyltetrahydro-3aH-cyclopenta[d][1,3]dioxol-4-yl)methanol hydrochloride (209.0 g) and then triethylamine (2103 mL) was added. The reaction was then heated to 80° C., under a blanket of nitrogen. After 360 minutes, HPLC analysis indicated that the reaction mixture contained <1% starting material and the reaction was cooled to 20° C. over 60 minutes. To the reaction was added ethyl acetate (3.5 L) and water (3.5 L). After stirring for 10 minutes the phases were separated and the aqueous layer was back extracted with ethyl acetate (3.5 L). The organic layers were combined and concentrated to form a dark, brown oil. Acetonitrile (4.5 L) was added and the solution was concentrated to dryness to give an orange solid. The solids was transferred back to the reaction with water (4.3 L), heated to 50° C., and stirred for 20 minutes. White solids formed in this hot solution and were isolated by filtration using a Nutche Filter over 15 minutes. The solids were dried under vacuum for 15 minutes on the filter and then dissolved in acetonitrile (4.0 L) at 50° C. The solution was stirred for 15 minutes. The solution was then filtered through a fritted funnel to remove the hydrolysis solid by product and the solution was concentrated to dryness. The solids were dried in a vacuum oven at full vacuum overnight (40° C., 16 hours). The reaction was then analyzed by HPLC and NMR to give ((3aR,4R,6R,6aS)-2,2-dimethyl-6-((2-(3-((trifluoromethyl)thio)phenyl)pyrazolo[1,5-a]pyrimidin-7-yl)amino)tetrahydro-3aH-cyclopenta[d][1,3]dioxol-4-yl)methanol (349.2 g, 88%). $^1$H NMR (300 MHz, DMSO-$d_6$) δ ppm 1.25 (s, 3H) 1.47 (s, 3H) 1.76-1.90 (m, 1H) 2.25 (br d, J=3.22 Hz, 1H) 2.33-2.47 (m, 1H) 3.46-3.67 (m, 2H) 4.08 (br d, J=5.57 Hz, 1H) 4.48-4.64 (m, 2H) 5.19 (t, J=4.40 Hz, 1H) 6.28 (d, J=5.28 Hz, 1H) 7.06 (s, 1H) 7.58-7.71 (m, 1H) 7.72-7.80 (m, 1H) 8.12-8.24 (m, 2H) 8.31 (d, J=7.62 Hz, 1H) 8.42 (s, 1H).

Step 5: ((3aR,4R,6R,6aS)-2,2-dimethyl-6-((2-(3-((trifluoromethyl)thio)phenyl)pyrazolo[1,5-a]pyrimidin-7-yl)amino)tetrahydro-3aH-cyclopenta[d][1,3]dioxol-4-yl)methyl tert-butoxycarbonylsulfamate ((3aR,4R,6R,6aS)-2,2-dimethyl-6-((2-(3-((trifluoromethyl)thio)phenyl)pyrazolo[1,5-a]pyrimidin-7-yl)amino)tetrahydro-3aH-cyclopenta[d][1,3]dioxol-4-yl)methanol (6.0 g) was dissolved in 2-methyltetrahedrafuran (60.0 mL) and to this solution was added pyridinium p-toluenesulfonate (5.9 g). This formed a precipitated and to this white slurry was added (4-aza-1-azoniabicyclo[2.2.2]oct-1-ylsulfonyl) (tert-butoxycarbonyl)azanide-1,4-diazabicyclo[2.2.2]octane (1:1) hydrochloride$^i$ (17.0 g). The mixture was stirred at ambient temperature until the HPLC showed <1% ((3aR, 4R,6R,6aS)-2,2-dimethyl-6-((2-(3-((trifluoromethyl)thio) phenyl)pyrazolo[1,5-a]pyrimidin-7-yl)amino)tetrahydro-3aH-cyclopenta[d][1,3]dioxol-4-yl)methanol remaining starting material (~300 minutes). The reaction was quenched with water (60 mL) and the phases were separated. To the organic layer was added acetonitrile (60 mL) and the mixture was concentrated using a rotovap at 50° C. to ~60 mL. The mixture was allowed to cool to room temperature and stirred overnight. During this time a white slurry formed. White solids were filtered using a medium fritted filter. The solid was dried in a vacuum oven at full vacuum overnight (40° C.). The reaction was then analyzed by HPLC and NMR to give ((3aR,4R,6R,6aS)-2,2-dimethyl-6-((2-(3-((trifluoromethyl)thio)phenyl)pyrazolo pyrimidin-7-yl)amino) tetrahydro-3aH-cyclopenta[d][1,3]dioxol-4-yl)methyl tert-butoxycarbonylsulfamate (5.03 g, 68%). NMR (300 MHz, DMSO-$d_6$) δ ppm 1.26 (s, 3H) 1.42 (s, 9H) 1.51 (s, 3H) 2.33-2.48 (m, 2H) 3.30 (br s, 1H) 4.06-4.21 (m, 1H) 4.29 (d, J=5.28 Hz, 2H) 4.52 (dd, J=7.18, 5.13 Hz, 1H) 4.76 (dd, J=7.18, 4.54 Hz, 1H) 6.35 (d, J=5.57 Hz, 1H) 7.08 (s, 1H) 7.63-7.72 (m, 1H) 7.74-7.82 (m, 1H) 8.01 (d, J=7.92 Hz, 1H) 8.21 (d, J=5.28 Hz, 1H) 8.31 (dt, J=7.84, 1.36 Hz, 1H) 8.48 (s, 1H) 11.92 (br s, 1H)

Step 6: ((1R,2R,3S,4R)-2,3-dihydroxy-4-((2-((3-((trifluoromethyl)thio)phenyl)pyrazolo[1,5-a]pyrimidin-7-yl)amino)cyclopentyl)methyl sulfamate To a solution of ((3aR,4R,6R,6aS)-2,2-dimethyl-6-((2-(3-((trifluoromethyl)thio)phenyl)pyrazolo[1,5-a]pyrimidin-7-yl)amino)tetrahydro-3aH-cyclopenta[d][1,3]dioxol-4-yl) methyl tert-butoxycarbonylsulfamate (2.0 g) in acetonitrile (11 mL) at 0° C. was added phosphoric acid (11 mL) while maintaining the temperature below 10° C. This mixture was warmed to ambient temperature and stirred for 4 hours. At this time HPLC analysis showed that <1% ((3aR,4R,6R, 6aS)-2,2-dimethyl-6-((2-(3-((trifluoromethyl)thio)phenyl) pyrazolo[1,5-b]pyrimidin-7-yl)amino)tetrahydro-3aH-cyclopenta[d][1,3]dioxol-4-yl)methyl tert-butoxycarbonylsulfamate starting material or reaction intermediates remained. To the reaction was added ethyl acetate (11 mL) and water (11 mL) and saturated $Na_2CO_3$ (10 mL) dropwise. After this addition was complete saturated $Na_2CO_3$ was added until the pH was between 6-7. The phases were separated and to the organic layer was added acetonitrile (30 mL) and the mixture was concentrated on a rotovap to ~16 mL. The mixture was stirred overnight. During this time a white slurry formed. The white solids were filtered using a medium flitted filter. The solid was dried in a vacuum oven at full vacuum overnight (40° C.). The reaction was then analyzed by HPLC and NMR to give ((1R,2R,3S,4R)-2,3-dihydroxy-4-((2-(3-((trifluoromethyl) thio)phenyl)pyrazolo[1,5-a]pyrimidin-7-yl)amino)cyclopentyl)methyl sulfamate (1.5 g, 84%). $^1$H NMR (300 MHz, DMSO-$d_6$) δ ppm 1.44-1.61 (m, 1H) 2.20-2.42 (m, 2H) 3.78 (q, J=4.50 Hz, 1H) 3.90-4.09 (m, 3H) 4.09-4.22 (m, 1H) 4.80 (d, J=5.28 Hz, 1H) 5.03 (d, J=5.28 Hz, 1H) 6.31 (d, J=5.57 Hz, 1H) 7.05 (s, 1H) 7.48 (s, 2H) 7.62-7.72 (m, 1H) 7.77 (d, J=7.92 Hz, 2H) 8.17 (d, J=5.28 Hz, 1H) 8.31 (dt, J=7.70, 1.43 Hz, 1H) 8.47 (s, 1H).

Example 3: ((1R,2R,3S,4R)-2,3-dihydroxy-4-((2-(3-((trifluoromethyl)thio)phenyl)pyrazolo[1,5-a]pyrimidin-7-yl)amino)cyclopentyl)methyl sulfamate Step 1: (2,2-dimethyl-5-(((3-(3-((trifluoromethyl) thio)phenyl)-1H-pyrazol-5-yl)amino)methylene)-1,3-dioxane-4,6-dione)

Under a blanket of nitrogen at 20° C., Meldrum's acid (18.6 Kg) and isopropanol (33 L) were placed in a 100 L glass-lined reactor. Trimethyl orthoformate (15.5 Kg (16.0 L)) and isopropanol (11 L) were added and the mixture was heated to 80° C. for 40 min, whereby a small amount of methanol distilled off (<0.5 L). The mixture was stirred for 2 h at 80° C. In a separate 160 L glass-lined reactor under nitrogen at 20° C., 3-(3-((trifluoromethyl)thio)phenyl)-1H-pyrazol-5-amine (prepared in the manner described above) was mixed with isopropanol (10.9 kg, 42.0 mmol) and heated up to 80° C. within 60 min. The content of the 100 L reactor was transferred into the reaction mixture in the 160 L reactor at 80° C., which was completed after 3 min. The reaction mixture was stirred for 30 min at 78° C., the reaction was then cooled to 60° C. HPLC analysis showed the reaction was 99.56% complete (product %/(product %+starting material %). The reaction mixture was cooled to 20° C. within 100 min, then the mixture was stirred for further 100 min at 20° C. The suspension was then transferred onto a pressure filter. At 1.2 bar nitrogen, the solids were collected on the filter. The filter cake was washed 4× with ethyl acetate (18 L each time). The wet cake was dried on the filter for 17 h at 20° C. using a slight stream of nitrogen/vacuum (200-100 mbar). The wet product (14.7 kg) was further dried at the rotavap for approx. 24 h at 40-50° C. 11.75 kg of the crude title compound was obtained (68% yield). NMR spectrum was consistent with that described above in Example 2.

Step 2: 2-(3-((trifluoromethyl)thio)phenyl)pyrazolo[1,5-a]pyrimidin-7-ol

Under nitrogen at 20° C., (2,2-dimethyl-5-(((3-(3-((trifluoromethyl)thio)phenyl)-1H-pyrazol-5-yl)amino)methylene)-1,3-dioxane-4,6-dione) was placed in the reactor. 1,2-Dichlorobenzene (117 L) was added. The suspension was heated to 147° C. for 90 min to give a solution, then it was stirred at 147° C. for 18 h. Before sampling, the reaction was cooled to 60° C. HPLC analysis showed the reaction was 92.28% completion (product %/(product %+starting material %). The mixture was heated up again to 147° C. and stirred for further 5 h at this temperature. HPLC analysis showed the reaction was 96.51% complete (product %/(product %+starting material %). The mixture was then stirred for 48 hours at 20° C., then it was heated again to 147° C. and stirred at this temperature for 5 h. Before sampling, the reaction was cooled to 60° C. HPLC analysis showed the reaction was 98.47% completion (product %/(product %+starting material %). The mixture was heated up again to 146° C. and stirred for further 5 h at this temperature. Before sampling, the reaction was cooled to 60° C. HPLC analysis showed the reaction was 99.35% complete (product %/(product %+starting material %). The reaction was cooled to 20° C. and the suspension was transferred in a pressure filter. The solids were collected on the filter at 1.8-3 bar $N_2$ over a greater than 10 hour period. The filter cake was washed 4× with acetonitrile (17 L), then it was dried on the filter for 18 h at 20° C./200-100 mbar, using a slight stream of $N_2$. The material was transferred to a 50 L flask and dried on a rotavap at 50-60° C./24-14 mbar for 2 d. 6.118 kg of the crude title compound was obtained (70% yield). NMR spectrum was consistent with that described above in Example 2.

Step 3: 1-(2-(3-((trifluoromethyl)thio)phenyl)pyrazolo[1,5-a]pyrimidin-7-yl)-1H-benzo[d][1,2,3]triazole:triethylamine:hydrochloride complex (1:0.21:0.21 moles:moles:moles)

Under $N_2$ at 20° C., acetonitrile (30 L) was placed in the reactor, 2-(3-((trifluoromethyl)thio)phenyl)pyrazolo[1,5-a]pyrimidin-7-ol (6.00 kg) and 1H-benzotriazol (5.83 kg) was added. A further portion of acetonitrile (30 L) was added, then the mixture was stirred at 20° C. Stirring proceeded over night. Triethylamine (8.16 L) was added at 20° C. over 6 min. The yellow suspension was heated up to 45° C. for 40 min. While stirring at 150 rpm, phosphoryl chloride (4.562 kg) was slowly added for 45 min. By controlling the addition, the reagent was dropped directly into the mixture to avoid the formation of lumps. The addition was exothermic, a maximum temperature of 53° C. was observed. The brown suspension was heated up to 80° C. over 1 h, then the reaction mixture was stirred for 5 h at this temperature. Acetonitrile (30 L) was added over 20 min keeping the internal temperature between 75-80° C. HPLC analysis showed the reaction was 98.31% completion (product %/(product %+starting material %). The mixture (brown suspension) was further stirred at 80° C. for 70 min. HPLC analysis showed the reaction was 99.48% completion (product %/(product %+starting material %). Acetonitrile (61 L) was added over 30 min maintaining the temperature between 75-80° C. The pale brown suspension was stirred at 80° C. for 90 min, then it was cooled to 20° C. over 2.5 h. The mixture was stirred for 12 h at 20° C. The mixture was transferred in a pressure filter. The filter cake was washed twice with acetonitrile (18 L). Both wash steps were done at 3.5-4 bar $N_2$. Each of these filtrations took overnight to go to completion. The filter cake was dried on the filter for 7.5 h. The material was transferred in a 50 L flask and dried at the rotavap at Ta 40-50° C./50-11 mbar for 3 d to get a dry mass of 99.88%. The yield of 1-(2-(3-((trifluoromethyl)thio)phenyl)pyrazolo[1,5-a]pyrimidin-7-yl)-1H-benzo[d][1,2,3]triazole:triethylamine:hydrochloride complex (1:0.21:0.21 moles:moles:moles) was 7.948 kg (75%). NMR spectrum was consistent with that described above in Example 2.

Step 4: ((3aR,4R,6R,6aS)-2,2-dimethyl-6-((2-(3-((trifluoromethyl)thio)phenyl)pyrazolo[1,5-a]pyrimidin-7-yl)amino)tetrahydro-3aH-cyclopenta[d][1,3]dioxol-4-yl)methanol Under $N_2$ in a 160 L glasslined reactor, triethylamine (21%) compound with 1-(2-(3-((trifluoromethyl)thio)phenyl)pyrazolo[1,5-a]pyrimidin-7-yl)-1H-benzo[d][1,2,3]triazole (21%) hydrochloride (7.86 kg) was dissolved in triethylamine (23.3 L) at 20° C. ((3aR,4R,6R,6aS)-6-amino-2,2-dimethyltetrahydro-3aH-cyclopenta[d][1,3]dioxol-4-yl)methanol hydrochloride (4.49 kg) was added, followed by triethylamine (23 L). The reaction mixture was heated up to 80° C. over 1 h, and then the mixture was stirred for 8 h at 80° C. The mixture was then cooled to 20° C. HPLC analysis showed the reaction was 99.97% complete (product %/(product %+starting material %). Water (66 L) was then added over 30 min at 20-25° C. (exotherm), whereby a brown suspension was obtained. The mixture was concentrated at 60° C., 150-95 mbar, until 42 L solvent was distilled off. The suspension was heated to 50° C., and the solids were collected on a 90 L pressure filter (1.2 bar $N_2$), which took 40 min. During this process, the material on the filter was not actively heated. The remaining solids in the reactor were rinsed with 15 L of the mother liquor. The wet filter cake was transferred back in the reactor. Water (64 L) was added. The mixture was heated up to 50° C. over 30 min. The washed solids were collected on the 90 L pressure filter. Remaining mother liquor in the filter cake was pressed off at 1.2 bar $N_2$ for 50 min (50 L mother liquor was used to rinse the reactor). The filter cake was dried on the pressure filter for 13.5 h, applying a slight stream of $N_2$/vac at 20° C. to afford 10.247 kg of crude ((3aR,4R,6R,6aS)-2,2-dimethyl-6-((2-(3-((trifluoromethyl)thio)phenyl)pyrazolo[1,5-a]pyrimidin-7-yl)amino)tetrahydro-3aH-cyclopenta[d][1,3]dioxol-4-yl)methanol. The wet filter cake was isolated. The wet filter cake was loaded into the reactor. Acetonitrile (65 L) was added, followed by activated charcoal (6.59 kg). The mixture was heated to 50° C. for 30 min and stirred for 2 h at 50° C. Meanwhile a bed of celite (4.25 kg) had been prepared in the 90 L pressure filter, using acetonitrile (20 L) for conditioning. The bed was heated at 50° C. The black suspension was transferred on the filter and pushed through the Celite plug at 2 bar. The filtrate was transferred to a 200 L stirring tank via a heat resistant tube and a 0.45 μm inline filter. The operation needed 18 min for completion. For washing, acetonitrile (50 L) which had been warmed up in the reactor to 50° C. and transferred over the warmed filter cake and pushed through at 2 bar. Again, the filtrate was transferred in the 200 L stirring tank via a heat resistant tube and a 0.45 μm inline filter. The operation needed 10 min for completion. The reactor was cleaned to remove attached charcoal (abrasive cleaning, using NaCl/acetone). The filtrate in the stirring tank was transferred in the reactor and concentrated at 50° C./120 mbar until 63 L were distilled off. While well stirring (300 rpm) and 50° C., Water (110 L) was slowly added over 2 h. A pale yellow suspension was formed. The concentrate was cooled to 20° C. for 3 h, then stirred at this temperature for 13 h. The solids were collected on a 50 L filter, using 1.2 bar $N_2$ to push the filtrate through. The filter cake was washed twice with water (18 L), then dried on the filter for 24 h at 200-100 mbar, using a slight stream of $N_2$. 4.563 kg of the title compound was obtained 55% yield. NMR spectrum was consistent with that described above in Example 2.

Step 5: ((3aR,4R,6R,6aS)-2,2-dimethyl-6-((2-(3-((trifluoromethyl)thio)phenyl)pyrazolo[1,5-a]pyrimidin-7-yl)amino)tetrahydro-3aH-cyclopenta[d][1,3]dioxol-4-yl)methyl tert-butoxycarbonylsulfamate Under $N_2$ at 20° C., ((3aR,4R,6R,6aS)-2,2-dimethyl-6-((2-(3-((trifluoromethyl)thio)phenyl)pyrazolo[1,5-a]pyrimidin-7-yl)amino)tetrahydro-3aH-cyclopenta[d][1,3]dioxol-4-yl)methanol (4.019 kg) was placed in a 160 L glasslined reactor, then 2-methyl-tetrahydrofuran (40 L) was added. The mixture was stirred at 150 rpm for 30 min at 20° C., whereby a clear solution was formed. A KF measurement was taken and showed the water content to be 0.036% $H_2O$. The solution was stirred over night at 20° C. The next morning, PPTS (2.2 kg) was loaded into the reactor. At 20° C., (4-aza-1-azoniabicyclo[2.2.2]oct-1-ylsulfonyl)(tert-butoxycarbonyl)azanide-1,4-diazabicyclo[2.2.2]octane (1:1) hydrochloride (10.2 kg) was added. Stirring of the heterogeneous mixture was started at 130 rpm. The reaction was stirred with 200 rpm for 1 h at 20° C., then with increased speed of 250 rpm for an additional hour. HPLC analysis showed the conversion to be 87.3%. The reaction mass was stirred with 300 rpm for 2 h at 20° C. HPLC analysis showed the conversion to be 95.6%. The reaction mass was stirred with 300 rpm for 2 h at 20° C. HPLC analysis showed the conversion to be 97.7%. NaHCO$_3$ 3.7% (40 L) was added to the mixture at 20° C. and the reaction was stirred at 300 rpm for 10 min. Most of the solids from the reaction mixture went into solution. To dissolve remaining material which was attached at the top of the reactor, the bilayered mixture was stir up shortly by a $N_2$ stream from the bottom. The layers were separated, which was completed after 13 min. The aqueous layer was discharged, the organic layer remained in the reactor. The org. layer was a brown solution, the aqueous layer was colorless and turbid. The pH of aqueous layer was approx. 8 (pH stick). NaHCO$_3$ 3.7% (40 L) was added to the mixture at 20° C. and it was stirred at 300 rpm for 10 min. The layers were separated, which was completed after 27 min. The aqueous layer was discharged, the organic layer remained in the reactor. The organic layer was a brown solution, the aqueous layer was colorless and turbid. The pH of aqueous layer was approx. 8-9 (pH stick) and the pH of organic layer was approx. 8 (pH stick, wet). The product in organic layer was transferred in the feeding tank and stored temporarily (approx. 30 min) at 20° C. The reactor was optically cleaned using a mixture of 2-methyl-tetrahydrofuran (30 L) and $H_2O$ (20 L). The org. layer was placed in the reactor and stored at −20° C. for 14.5 h. While stirring at 150 rpm, the org. layer (suspension) was diluted with acetonitrile (16 L) and water (15 L) and warmed up to 5° C. At 5° C., acetic acid (0.172 kg) was added over 5 min. to a pH of 6; resulting in a mixture that was a pale brown solution. ((3aR,4R,6R,6aS)-2,2-dimethyl-6-((2-(3-((trifluoromethyl)thio)phenyl)pyrazolo[1,5-a]pyrimidin-7-yl)amino)tetrahydro-3aH-cyclopenta[d][1,3]dioxol-4-yl) methyl tert-butoxycarbonylsulfamate (2.0 g; prepared in a similar manner to that described above Example 2, Step 5) was added as seed. At 5° C., acetic acid (0.515 kg) was added over 15 min. to pH 4-5; a suspension formed. The feeding tank was rinsed with water (1.6 L). The mixture was stirred at 5° C. with 90 rpm for 1.5 h, then it was transferred in a 50 L filter and filtered at 1.2 bar $N_2$, in only 4 min. The filter cake was washed 4× with cold acetonitrile (8 L, 0-5° C.), then it was dried on the filter at 20° C. for 8 h at 200 mbar, using a slight stream of $N_2$. The yield of the title compound was 3.594 kg (62%). NMR spectrum was consistent with that described above in Example 2.

Step 6: ((1R,2R,3S,4R)-2,3-dihydroxy-4-((2-(3-((trifluoromethyl)thio)phenyl)pyrazolo[1,5-a]pyrimidin-7-yl)amino)cyclopentyl)methyl sulfamate Compound 1

3.538 kg of ((3aR,4R,6R,6aS)-2,2-dimethyl-6-((2-(3-((trifluoromethyl)thio)phenyl)pyrazolo[1,5-a]pyrimidin-7-yl)amino)tetrahydro-3aH-cyclopenta[d][1,3]dioxol-4-yl) methyl tert-butoxycarbonylsulfamate was suspended in 13.5 kg of acetonitrile and cooled to 5° C. To this mixture was added 27.3 kg of $H_3PO_4$ over 1 hour and 50 minutes. The reaction was warmed to 20° C. over 50 minutes and then stirred for 8 h at 22° C. HPLC analysis showed the reaction was 99.69% complete. To the first portion (50% of the reaction mixture) was added 8.9 kg of water and 7.95 kg of ethyl acetate. The pH was then adjusted to 6.5 with 48 L of saturated sodium carbonate. 7.7 kg of ethyl acetate was added and the phases were separated. To the second portion (50% of the reaction mixture) was added 8.9 kg of water and 7.95 kg of ethyl acetate. The pH was then adjusted to 6.15 with 48 L of saturated sodium carbonate. 7.7 kg of ethyl acetate was added and the phases were separated. The organic phases were combined in a vessel (rinsed with 1.8 kg of ethyl acetate) and washed with 17.8 kg of water. The phases were separated and 17.8 kg of water and 0.237 kg of NaCl were added and the phases were separated. A repeat of wash with 17.8 kg of water and 0.237 kg of NaCl was added and the phases were separated. The organic layers were then combined and the temperature of the mixture was raised to 40° C. and the pressure was reduced to 300-142 mbar. 27 L of liquid was distilled off over 4 h. 31.7 kg of acetonitrile were then added to the solution and the temperature of the mixture was raised to 38° C. and the pressure was reduced to 320-153 mbar. 26 L of liquid was distilled over 3 h. 31.7 kg of acetonitrile were then added to the solution and the temperature of the mixture was raised to 37° C. and the pressure was reduced to 320-153 mbar. 34 L of liquid was distilled over 2 h. The suspension was stirred for 1 h at 50° C. and then cooled to 20-25° C. over 3 h. The reaction was stirred overnight and the product was filtered and washed with 8.9 kg of acetonitrile twice. The cake was dried for 2 h at 20° C. (33 mbar) then at 40-45° C. (1 mbar) to afford 2.08 kg (75.8%) of the title compound. 2.066 kg of ((1R, 2R,3S,4R)-2,3-dihydroxy-4-((2-(3-((trifluoromethyl)thio) phenyl)pyrazolo[1,5-a]pyrimidin-7-yl)amino)cyclopentyl)

methyl sulfamate was loaded into a reactor with 9.76 kg of acetonitrile and 4.12 kg of water and heated at a temperature of 56° C. for 1 hour and 10 minutes until dissolved. The solution was polished filtered and the filter was rinsed with 3.16 kg acetonitrile and 1.37 kg of water. To the resulting solution was added with 11.0 kg of water over 45 minutes while maintaining the reaction temperature between 52-55° C. 0.009 kg of ((1R,2R,3S,4R)-2,3-dihydroxy-4-((2-(3-((trifluoromethyl)thio)phenyl)pyrazolo[1,5-a]pyrimidin-7-yl)amino)cyclopentyl)methyl sulfamate was added as seed (prepared in a similar manner to that described above Example 2, Step 5). A suspension was visible after 10 minutes of stirring. To the solution was added 9.62 kg of water over 3 h while maintaining the reaction temperature between 50-55° C. The suspension was then cooled over 3 h to 20° C. and stirred for 12 h at 22-23° C. The suspension was then filtered and washed twice with 13.7 kg of water. The product was dried at 40° C. 1.605 kg of the title compound was obtained in 78% yield. NMR spectrum was consistent with that described above in Example 2.

Example 4: In Vivo Tumor Efficacy Models

The HN-13-0014 xenograft model is a human head and neck primary tumor model. Approximately nine week old female BALB/c nude (Shanghai Sino-British SIPPR/BK Laboratory Animal Co., LTD.) mice were implanted subcutaneously with approximate 30 mm$^3$ HN-13-0014 tumor slices in the right flank. When the mean tumor volume reached approximately 162 mm$^3$, the animals were randomized into 10 treatment groups (n=8/group).

The LU-01-0030 xenograft model is a human primary non-small cell lung cancer model. In the first study with the LU-01-0030 model, approximately nine week old female BALB/c nude (Shanghai Sino-British SIPPR/BK Laboratory Animal Co., LTD.) mice were implanted subcutaneously with approximate 30 mm$^3$ LU-01-0030 tumor slices in the right flank. When the mean tumor volume reached approximately 159 mm$^3$, the animals were randomized into 10 treatment groups (n=8/group).

In a second study with the LU-01-0030 xenograft model, 6-8 week old female BALB/c nude (Shanghai Sino-British SIPPR/BK Laboratory Animal Co., LTD.) mice were implanted subcutaneously with approximate 20-30 mm$^3$ LU-01-0030 tumor slices in the right flank. When the mean tumor volume reached approximately 182 mm$^3$, the animals were randomized into 6 treatment groups (n=8/group).

The LU-01-0266 xenograft model is a human primary non-small cell lung tumor model. Approximately nine week old female BALB/c nude (Shanghai Sino-British SIPPR/BK Laboratory Animal Co., LTD.) mice were implanted subcutaneously with approximate 30 mm$^3$ LU-01-0266 tumor slices in the right flank. When the mean tumor volume reached approximately 173 mm$^3$, the animals were randomized into 10 treatment groups (n=8/group).

The ST-02-0004 xenograft model is a human primary gastric cancer model. Approximately nine week old female BALB/c nude (Shanghai Sino-British SIPPR/BK Laboratory Animal Co., LTD.) mice were implanted subcutaneously with approximate 30 mm$^3$ ST-02-0004 tumor slices in the right flank. When the mean tumor volume reached approximately 162 mm$^3$, the animals were randomized into 6 treatment groups (n=8/group).

The HN-13-0007 xenograft model is a human primary head and neck lung cancer model. Approximately nine week old female BALB/c nude (Shanghai Sino-British SIPPR/BK Laboratory Animal Co., LTD.) mice were implanted subcutaneously with approximate 30 mm$^3$ HN-13-0007 tumor slices in the right flank. When the mean tumor volume reached approximately 130 mm$^3$, the animals were randomized into 10 treatment groups (n=8/group).

Test Agents

The test agents were administered as outlined below.

Compound 1 [((1R,2R,3S,4R)-2,3-dihydroxy-4-(2-(3-(trifluoromethylthio)¬ phenyl)pyrazolo[1,5-a]pyrimidin-7-ylamino)cyclopentyl)methyl sulfamate] is formulated in 10% HPbCD in sterile water and administered intravenously on a BIW (twice/week schedule; Monday and Thursday, i.e. days 0, 3, 7, 10, 14, 17) for 3 weeks in the HN-13-0014 and LU-01-0030 (first study) models. Compound 1 formulation was prepared weekly and stored at room temperature in the dark.

Compound 1 [((1R,2R,3S,4R)-2,3-dihydroxy-4-(2-(3-(trifluoromethylthio)¬ phenyl)pyrazolo[1,5-a]pyrimidin-7-ylamino)cyclopentyl)methyl sulfamate] is formulated in 10% HPbCD in sterile water and administered intravenously on days 0, 3, 7, 10, 14, 17 in the LU-01-0266 and HN-13-0007 models and on days 0, 3, 8, 11, 15, 18 in the ST-02-0004 model and in the second study with the LU-01-0030 model. Compound 1 formulation was prepared weekly and stored at room temperature in the dark.

Beam-focused radiation was delivered using a either 1 or 2 Gray dosed on days 0, 1, 7, and 8 or on days 0, 3, 7, and 10 in the HN-13-0014 and LU-01-0030 (first study) models. A Rad Source RS-2000 X-ray irradiator was used for therapy (Rad Source). Before radiation, animals were anesthetized by i.p. injection using 1.0% sodium pentobarbital at 80 mg/kg (Vendor: Sigma). Focused radiation was applied to each mouse at 1 Gy/min.

Beam-focused radiation was delivered using 2 Gray dosed on days 0, 1, 7, and 8 or on days 0, 3, 7, and 10 in the LU-01-0266 and HN-13-0007 models. In the ST-02-0004 model 2 Gray of radiation was delivered on days 0, 1, 3, and 8. A Rad Source RS-2000 X-ray irradiator was used for therapy (Rad Source). Before radiation, animals were anesthetized by i.p. injection using 1.0% sodium pentobarbital at 80 mg/kg (Vendor: Sigma). Focused radiation was applied to each mouse at 1 Gy/min.

Beam-focused radiation was delivered using 4 Gray dosed on day 0 in the second study for the LU-01-0030 model.

Tumor Measurements:

Tumors were measured twice weekly using vernier calipers. Tumor volumes were calculated using the following formula: $(0.5 \times [length \times width^2])$. Treatment groups and dosing/treatment schedules are indicated in Tables 1a, 2a, 3a, 4a, and 5a below. Tumor size and body weight are measured approximately twice a week for the duration of the study. Mice are euthanized when their tumor volume reached approximately 1000 mm$^3$. Tumor growth continued to be monitored after the dosing period in some studies. In Tables 1a, 2a, 3a, 4a, and 5a tumor volumes are shown for HN-13-0014 (day 21), LU-01-0030 (day 21), the second LU-01-0030 study (day 20), LU-01-0266 (day 20), ST-02-0004 (day 21) and FIN-13-0007 (day 24), respectively. Average tumor volume is reported as a function of time for selected groups of selected studies.

Statistical Analyses of Combination Effect for Tumor Growth in Subcutaneous Xenograft Models Measurements from day 0 to day 20, day 21 or day 24 are analyzed as specified in Tables below. All tumor volumes have a value of 1 added to them before $\log_{10}$ transformation. For each animal, the log tumor volume at day 0 is subtracted from the log tumor volume on the subsequent days. This difference vs. time is used to calculate an area under the curve (AUC) for each animal using the trapezoid rule. In instances when an animal in a treatment group is removed early from the study, the last observed tumor value is carried forward through all subsequent time points. The synergy score for the combination of agents A and B is defined as $$100*(\text{mean}(AUC_{AB})-\text{mean}(AUC_A)-\text{mean}(AUC_B)+\text{mean}(AUC_{ctl}))/\text{mean}(AUC_{ctl}):$$

where $AUC_{AB}$, $AUC_A$, $AUC_B$, and $AUC_{ctl}$ are the AUC values for animals in the combination group, the A group, the B group, and the control group, respectively. The standard error of the synergy score is computed based on the variation in the AUC values among the animals. A two sided t-test is used to determine if the synergy score is significantly different from zero. If the P-value is above 0.05, then the combination is considered to be additive. If the P-value is below 0.05, and the synergy score is less than zero, then the combination is considered to be synergistic. If the P-value is below 0.05 and the synergy score was greater than zero, but the mean AUC for the combination was lower than the lowest mean AUC among the two single agent treatments, then the combination was sub-additive. If the P-value is below 0.05 and if the synergy score was greater than zero, and the mean AUC for the combination was greater than the mean AUC for at least one of the single agent treatments, then the combination was antagonistic.

Results

Mouse xenograft models, performed as described in the general methods above, were used to assess the combination effect in vivo of Compound 1 combined with radiation. The details for each study are as shown below in Tables 1a, 2a, 3a, 4a, and 5a. The results were analyzed using the statistical analysis described above and the classification of the combination is shown below in Tables 1b, 2b, 3b, 4b, and 5b.

HN-13-0014 Xenograft Model

In the HN-13-0014 model, dosing of the single agents Compound 1 (IV at 6.25 and 15 mg/kg BIW for 3 weeks) or radiation (2 Gy on study days 0, 1, 7, 8 or days 0, 3, 7, 10) yielded modest anti-tumor activity compared to vehicle control. Combining Compound 1 with 2 Gy radiation yielded an additive combination effect. All treatment groups from the study are shown in Table 1a. The combination classification for this combination is shown in Table 1b. Tumor growth curves are shown during the treatment period (FIGS. 1a and 1b). Mean tumor growth curves for study group arms 1, 2, 3, 4, 6 and 8 are shown in FIG. 1a and Arms 1, 2 3, 5, 7 and 9 are shown in FIG. 1b. Error bars shown in FIGS. 1a and 1b indicate the standard error of the mean (SEM).

TABLE 1a

Combination of radiation and Compound 1 in the HN-13-0014 xenograft model

| Study Group | Treatment | Dosing Regimen | Route | Tumor Volume Day 21 | SEM Tumor Volume Day 21 | Number of mice in group (number on Day 21) |
|---|---|---|---|---|---|---|
| 1 | 10% HPbCD | BIWx3 | IV | 664.3 | 328.7 | 8 |
| 2 | 2 Gy Radiation | D 0, 1, 7, 8 | Beam | 428.8 | 163.3 | 8 |
| 3 | 2 Gy Radiation | D 0, 3, 7, 10 | Beam | 422.1 | 232.3 | 8 |
| 4 | 15 mg/kg Compound 1 | BIWx3 | IV | 539.9 | 202.7 | 8 |
| 5 | 6.25 mg/kg Compound 1 | BIWx3 | IV | 575.9 | 209.9 | 8 |
| 6 | 15 mg/kg Compound 1, 2 Gy Radiation | BIWx3, D 0, 1, 7, 8 | IV, Beam | 372.4 | 105.4 | 8 |
| 7 | 6.25 mg/kg Compound 1, 2 Gy Radiation | BIWx3, D 0, 1, 7, 8 | IV, Beam | 392.7 | 191 | 8 |
| 8 | 15 mg/kg Compound 1, 2 Gy Radiation | BIWx3, D 0, 3, 7, 10 | IV, Beam | 356.2 | 161.9 | 8 |
| 9 | 6.25 mg/kg Compound 1, 2 Gy Radiation | BIWx3, D 0, 3, 7, 10 | IV, Beam | 381.9 | 129.6 | 8 |
| 10 | 1 Gy Radiation | D 0, 3, 7, 10 | Beam | 530.9 | 230.8 | 8 |

TABLE 1b

Classification for in vivo combination of radiation and Compound 1 in the HN-13-0014 xenograft model

| Study group | Synergy score | SEM | P-value | Classification |
|---|---|---|---|---|
| 15 mg/kg Compound 1 + 2 Gy Radiation D0, 1, 7, 8 | 7.9 | 12.2 | 0.527 | Additive |
| 15 mg/kg Compound 1 + 2 Gy Radiation D0, 3, 7, 10 | 3.2 | 13.4 | 0817 | Additive |

TABLE 1b-continued

Classification for in vivo combination of radiation and Compound 1 in the HN-13-0014 xenograft model

| Study group | Synergy score | SEM | P-value | Classification |
|---|---|---|---|---|
| 6.25 mg/kg Compound 1 + 2 Gy Radiation D0, 1, 7, 8 | 8.6 | 10.6 | 0.434 | Additive |
| 6.25 mg/kg Compound 1 + 2 Gy Radiation D0, 3, 7, 10 | 7.7 | 8.6 | 0.379 | Additive |

LU-01-0030 Xenograft Model

In the first study using the LU-01-0030 model dosing 6.25 mg/kg Compound 1 as a single agent resulted in no antitumor activity compared to the vehicle control. Dosing single agents Compound 1 at 15 mg/kg or radiation (2 Gy on study days 0, 1, 7, 8 or days 0, 3, 7, 10) yielded tumor stasis. Combining Compound 1 with 2 Gy radiation yielded an additive-to-synergistic combination effect. All study groups from the study are shown in Table 2a. The combination effect for this combination is shown in Table 2b. Tumor growth curves are shown during the treatment period (FIGS. 2a, 2b, and 2c). Mean tumor growth curves for study group arms 1, 3, 4, and 8 are shown in FIG. 2a, arms 1, 2, 3, 4, 6 and 8 are shown in FIG. 2b, and arms 1, 2 3, 5, 7 and 9 are shown in FIG. 2c. The error bars shown on the FIGS. 2a, 2b, and 2c indicate the standard error measurements (SEM).

TABLE 2b

Classification for in vivo combination of Radiation and Compound 1 in the LU-01-0030 xenograft model

| Treatment | Synergy score | SEM | P-value | Classification |
|---|---|---|---|---|
| 15 mg/kg Compound 1 + 2 Gy Radiation D0, 1, 7, 8 | −139.6 | 40 | 0.004 | Synergy |
| 15 mg/kg Compound 1 + 2 Gy Radiation D0, 3, 7, 10 | −165.9 | 37.5 | 0.001 | Synergy |
| 6.25 mg/kg Compound 1 + 2 Gy Radiation D0, 1, 7, 8 | 5.4 | 24.7 | 0.830 | Additive |
| 6.25 mg/kg Compound 1 + 2 Gy Radiation D0, 3, 7, 10 | −22.2 | 23.2 | 0.356 | Additive |

In the second LU-01-0030 study using the model, combining Compound 1 with 4 Gy radiation yielded an additive combination effect. All study groups from the second LU-01-0030 study are shown in Table 2c. The combination effect for this combination is shown in Table 2d.

TABLE 2a

Combination of Radiation and Compound 1 in the LU-01-0030 xenograft model

| Study Group | Treatment | Dosing Regimen | Route | Tumor Volume Day 21 | SEM Tumor Volume Day 21 | Number of mice in group (number on Day 21) |
|---|---|---|---|---|---|---|
| 1 | 10% HPbCD | BIWx3 | IV | 572.3 | 163.1 | 8 |
| 2 | 2 Gy Radiation | D 0, 1, 7, 8 | Beam | 111.2 | 102.8 | 8 |
| 3 | 2 Gy Radiation | D 0, 3, 7, 10 | Beam | 112.4 | 52.4 | 8 |
| 4 | 15 mg/kg Compound 1 | BIWx3 | IV | 151.3 | 99.4 | 8 |
| 5 | 6.25 mg/kg Compound 1 | BIWx3 | IV | 555.7 | 160.5 | 8 |
| 6 | 15 mg/kg Compound 1, 2 Gy Radiation | BIWx3, D 0, 1, 7, 8 | IV, Beam | 2.3 | 6.4 | 8 |
| 7 | 6.25 mg/kg Compound 1, 2 Gy Radiation | BIWx3, D 0, 1, 7, 8 | IV, Beam | 101.9 | 114.9 | 8 |
| 8 | 15 mg/kg Compound 1, 2 Gy Radiation | BIWx3, D 0, 3, 7, 10 | IV, Beam | 2.8 | 7.8 | 8 |
| 9 | 6.25 mg/kg Compound 1, 2 Gy Radiation | BIWx3, D 0, 3, 7, 10 | IV, Beam | 106.3 | 83.3 | 8 |
| 10 | 1 Gy Radiation | D 0, 3, 7, 10 | Beam | 283.1 | 60.3 | 8 |

TABLE 2c

Combination of Radiation and Compound 1 in the second LU-01-0030 xenograft study

| Study Group | Treatment | Dosing Regimen | Route | Tumor Volume Day 20 | SEM Tumor Volume Day 20 | Number of mice in group (number on Day 20) |
|---|---|---|---|---|---|---|
| 1 | 10% HPbCD | D 0, 3, 8, 11, 15, 18 | IV | 947.2 | 116.3 | 8 |
| 2 | 4 Gy Radiation | D 0 | Beam | 251.5 | 39.0 | 8 |
| 3 | 15 mg/kg Compound 1 | D 0, 3, 8, 11, 15, 18 | IV | 67.8 | 25.7 | 8 |
| 4 | 6.25 mg/kg Compound 1 | D 0, 3, 8, 11, 15, 18 | IV | 648.9 | 121.0 | 8 |
| 5 | 15 mg/kg Compound 1, 4 Gy Radiation | D 0, 3, 8, 11, 15, 18; D 0 | IV, Beam | 2.04 | 2.1 | 8 |
| 6 | 6.25 mg/kg Compound 1, 4 Gy Radiation | D 0, 3, 8, 11, 15, 18; D 0 | IV, Beam | 83.8 | 36.5 | 8 |

TABLE 2d

Classification for in vivo combination of Radiation and Compound 1 in the second LU-01-0030 xenograft study

| Treatment | Synergy score | SEM | P-value | Classification |
|---|---|---|---|---|
| 15 mg/kg Compound 1 + 4 Gy Radiation D0 | −10.3 | 37.2 | 0.786 | Additive |
| 6.25 mg/kg Compound 1 + 4 Gy Radiation D0 | −74.5 | 33.3 | 0.052 | Additive |

LU-01-0266 Xenograft Model

In the LU-01-0266 model, dosing of Compound 1 (IV at 6.25 and 15 mg/kg BIW for 3 weeks on Days 0, 3, 7, 10, 14, 17) resulted in weak anti-tumor activity compared to the vehicle control. Dosing radiation (2 Gy on study days 0, 1, 7, 8 or days 0, 3, 7, 10) yielded strong anti-tumor activity compared to vehicle control. Combining Compound 1 with 2 Gy radiation yielded an additive combination effect. All treatment groups from the study are shown in Table 3a. The combination classification for this combination is shown in Table 3b. Mean tumor growth curves are shown in FIGS. 3a and 3b. Tumor growth curves are shown during the treatment period. Study group arms 1, 2, 3, 4, 6 and 8 are shown in FIG. 3a and Arms 1, 2 3, 5, 7 and 9 are shown in FIG. 3b. Error bars shown in FIGS. 3a and 3b indicate the standard error of the mean (SEM).

TABLE 3a

Combination of radiation and Compound 1 in the LU-01-0266 xenograft model

| Study Group | Treatment | Dosing Regimen | Route | Tumor Volume Day 20 | SEM Tumor Volume Day 20 | Number of mice in group (number on Day 20) |
|---|---|---|---|---|---|---|
| 1 | 10% HPbCD | BIWx3 = D 0, 3, 7, 10, 14, 17 | IV | 1255.6 | 545 | 8 |
| 2 | 2 Gy Radiation | D 0, 1, 7, 8 | Beam | 195.8 | 76.9 | 8 |
| 3 | 2 Gy Radiation | D 0, 3, 7, 10 | Beam | 187.5 | 100.5 | 8 |
| 4 | 15 mg/kg Compound 1 | BIWx3 = D 0, 3, 7, 10, 14, 17 | IV | 779 | 263.7 | 8 |
| 5 | 6.25 mg/kg Compound 1 | BIWx3 = D 0, 3, 7, 10, 14, 17 | IV | 1004.5 | 440.9 | 8 |
| 6 | 15 mg/kg Compound 1, 2 Gy Radiation | BIWx3 = D 0, 3, 7, 10, 14, 17 D 0, 1, 7, 8 | IV Beam | 77.4 | 42.3 | 8 |
| 7 | 6.25 mg/kg Compound 1, 2 Gy Radiation | BIWx3 = D 0, 3, 7, 10, 14, 17 D 0, 1, 7, 8 | IV Beam | 181.6 | 69.8 | 8 |
| 8 | 15 mg/kg Compound 1, 2 Gy Radiation | BIWx3 = D 0, 3, 7, 10, 14, 17 D 0, 3, 7, 10 | IV Beam | 174.9 | 102.8 | 8 |
| 9 | 6.25 mg/kg Compound 1, 2 Gy Radiation | BIWx3 = D 0, 3, 7, 10, 14, 17 D 0, 3, 7, 10 | IV Beam | 213.4 | 139.9 | 8 |

TABLE 3b

Classification for in vivo combination of radiation and Compound 1 in the LU-01-0266 xenograft model through Day 20

| Study group | Synergy score | SEM | P-value | Classification |
|---|---|---|---|---|
| 15 mg/kg Compound 1 + 2 Gy Radiation D0, 1, 7, 8 | −25 | 14 | 0.096 | Additive |
| 15 mg/kg Compound 1 + 2 Gy Radiation D0, 3, 7, 10 | 12 | 13 | 0.369 | Additive |
| 6.25 mg/kg Compound 1 + 2 Gy Radiation D0, 1, 7, 8 | 14 | 14 | 0.351 | Additive |
| 6.25 mg/kg Compound 1 + 2 Gy Radiation D0, 3, 7, 10 | 15 | 13 | 0.268 | Additive |

ST-02-0004 Xenograft Model

In the ST-02-0004 model dosing of Compound 1 (IV at 6.25 and 15 mg/kg for 3 weeks on Days 0, 3, 8, 11, 15 and 18) resulted in no significant anti-tumor activity compared to the vehicle control. Dosing Radiation (2 Gy on days 0, 1, 3, 8) yielded strong tumor growth inhibition compared to vehicle control. Combining Compound 1 at 6.25 mg/kg with 2 Gy of Radiation yielded an additive combination effect. In contrast, combining Compound 1 at 15 mg/kg with 2 Gy of Radiation yielded a synergistic combination effect. All study groups from the study are shown in Table 4a. The combination effect for this combination is shown in Table 4b. Tumor growth curves are shown during the treatment period (FIGS. 4a and 4b). Study group arms 1, 2, 4 and 6 are shown in FIG. 4a and arms 1, 2 3 and 5 are shown in FIG. 4b. The error bars shown in FIGS. 4a and 4b indicate the standard error of the mean (SEM).

TABLE 4b

Classification for in vivo combination of Radiation and Compound 1 in the ST-02-0004 xenograft model through Day 21

| Treatment | Synergy score | SEM | P-value | Classification |
|---|---|---|---|---|
| 15 mg/kg compound 1 + 2 Gy Radiation D0, 1, 3, 8 | −49 | 17 | 0.01 | Synergy |
| 6.25 mg/kg compound 1 + 2 Gy Radiation D0, 1, 3, 8 | 10 | 23 | 0.659 | Additive |

HN-13-0007 Xenograft Model

In the HN-13-0007 model dosing of Compound 1 (IV at 6.25 mg/kg for 3 weeks on Days 0, 3, 7, 10, 14, 17) resulted in no anti-tumor activity compared to the vehicle control. Dosing single agents Compound 1 at 15 mg/kg or radiation (2 Gy on study days 0, 1, 7, 8 or days 0, 3, 7, 10) yielded minimal tumor growth inhibition. Combining Compound 1 with 2 Gy radiation yielded an additive combination effect. All study groups from the study are shown in Table 5a. The combination effect for this combination is shown in Table 5b. Mean tumor growth curves are shown during the treatment period (FIGS. 5a and 5b). Study group arms 1, 2, 3, 4, 6 and 8 are shown in FIG. 5a and arms 1, 2, 3, 5, 7 and 9 are shown in FIG. 5b. Error bars shown in FIGS. 5a and 5b indicate the standard error of the mean (SEM).

TABLE 4a

Combination of Radiation and compound 1 in the ST-02-0004 xenograft model

| Study Group | Treatment | Dosing Regimen | Route | Tumor Volume Day 21 | SEM Tumor Volume Day 21 | Number of mice in group (number on Day 21) |
|---|---|---|---|---|---|---|
| 1 | 10% HPbCD | BIWx3 = D 0, 3, 8, 11, 15, 18 | IV | 660.8 | 65.4 | 8 |
| 2 | 2 Gy Radiation | D 0, 1, 3, 8 | Beam | 272.1 | 34.6 | 8 |
| 3 | 6.25 mg/kg compound 1 | BIWx3 = D 0, 3, 8, 11, 15, 18 | IV | 697.1 | 201.0 | 8 |
| 4 | 15 mg/kg compound 1 | BIWx3 = D 0, 3, 8, 11, 15, 18 | IV | 755.2 | 107.9 | 8 |
| 5 | 6.25 mg/kg compound 1, 2 Gy Radiation | BIWx3 = D 0, 3, 8, 11, 15, 18 D 0, 1, 3, 8 | IV Beam | 266.8 | 37.9 | 8 |
| 6 | 15 mg/kg compound 1, 2 Gy Radiation | BIWx3 = D 0, 3, 8, 11, 15, 18 D 0, 1, 3, 8 | IV Beam | 178.2 | 27.6 | 8 |

TABLE 5a

Combination of Radiation and Compound 1 in the HN-13-0007 xenograft model

| Study Group | Treatment | Dosing Regimen | Route | Tumor Volume Day 24 | SEM Tumor Volume Day 24 | Number of mice in group (number on Day 24) |
|---|---|---|---|---|---|---|
| 1 | 10% HPbCD | BIWx3 = D 0, 3, 7, 10, 14, 17 | IV | 424.4 | 247 | 8 |
| 2 | 2 Gy Radiation | D 0, 1, 7, 8 | Beam | 309.9 | 148.8 | 8 |
| 3 | 2 Gy Radiation | D 0, 3, 7, 10 | Beam | 345.2 | 161.2 | 8 |
| 4 | 15 mg/kg Compound 1 | BIWx3 = D 0, 3, 7, 10, 14, 17 | IV | 362.1 | 151.3 | 8 |
| 5 | 6.25 mg/kg Compound 1 | BIWx3 = D 0, 3, 7, 10, 14, 17 | IV | 442.4 | 153.4 | 8 |
| 6 | 15 mg/kg Compound 1, 2 Gy Radiation | BIWx3 = D 0, 3, 7, 10, 14, 17 D 0, 1, 7, 8 | IV Beam | 358.3 | 126.5 | 8 |
| 7 | 6.25 mg/kg Compound 1, 2 Gy Radiation | BIWx3 = D 0, 3, 7, 10, 14, 17 D 0, 1, 7, 8 | IV Beam | 318.8 | 112.6 | 8 |
| 8 | 15 mg/kg Compound 1, 2 Gy Radiation | BIWx3 = D 0, 3, 7, 10, 14, 17 D 0, 3, 7, 10 | IV Beam | 299.7 | 209.5 | 8 |
| 9 | 6.25 mg/kg Compound 1, 2 Gy Radiation | BIWx3 = D 0, 3, 7, 10, 14, 17 D 0, 3, 7, 10 | IV Beam | 340 | 190.4 | 8 |

TABLE 5b

Classification for in vivo combination of Radiation and Compound 1 in the HN-13-0007 xenograft model through Day 24

| Treatment | Synergy score | SEM | P-value | Classification |
|---|---|---|---|---|
| 15 mg/kg Compound 1 + 2 Gy Radiation D0, 1, 7, 8 | 24 | 26 | 0.355 | Additive |
| 15 mg/kg Compound 1 + 2 Gy Radiation D0, 3, 7, 10 | −13 | 23 | 0.584 | Additive |
| 6.25 mg/kg Compound 1 + 2 Gy Radiation D0, 1, 7, 8 | −20 | 21 | 0.354 | Additive |
| 6.25 mg/kg Compound 1 + 2 Gy Radiation D0, 3, 7, 10 | −24 | 22 | 0.287 | Additive |

TABLE 6

Number of HCT-116 Colonies Counted Per Well

| Washout | Radiation (Gray) | Compound 1 (nM) | Number of Colonies/well | | |
|---|---|---|---|---|---|
| No | 0 | 0 | 44 | 34 | 32 |
| No | 0 | 30 | 0 | 0 | 0 |
| No | 0 | 100 | 0 | 0 | 0 |
| No | 0 | 300 | 0 | 0 | 0 |
| No | 2 | 0 | 16 | 20 | 33 |
| No | 2 | 30 | 0 | 0 | 0 |
| No | 2 | 100 | 0 | 0 | 0 |
| No | 2 | 300 | 0 | 0 | 0 |
| No | 4 | 0 | 11 | 15 | 8 |
| No | 4 | 30 | 0 | 0 | 0 |
| No | 4 | 100 | 0 | 0 | 0 |
| No | 4 | 300 | 0 | 0 | 0 |
| Yes | 0 | 0 | 34 | 29 | 25 |
| Yes | 0 | 30 | 20 | 26 | 20 |
| Yes | 0 | 100 | 1 | 1 | 0 |
| Yes | 0 | 300 | 0 | 0 | 0 |
| Yes | 2 | 0 | 20 | 14 | 15 |
| Yes | 2 | 30 | 3 | 7 | 6 |
| Yes | 2 | 100 | 0 | 0 | 0 |
| Yes | 2 | 300 | 0 | 0 | 0 |
| Yes | 4 | 0 | 13 | 6 | 10 |
| Yes | 4 | 30 | 1 | 1 | 4 |
| Yes | 4 | 100 | 0 | 1 | 0 |
| Yes | 4 | 300 | 0 | 0 | 0 |

Example 5: In Vitro Colony Formation Assays

General Method: HCT-116 cells are grown in McCoy's 5A Medium supplemented with 10% fetal bovine serum. Cells are seeded (200/well) on a 12-well plate. The next day cells are treated with increasing concentrations of Compound 1 (in medium) and 2 hours later irradiated with 0, 2 or 4 gray. After an additional 6 hour, medium is replaced with and without (washout condition) Compound 1. After 10 days the number of colonies is counted and recorded. Radiator used is an X-ray irradiator (MBR-1520R-3, Hitachi Power Solutions Co., Ltd.).

Results:

Ten days following initiation of treatment, the number of HCT-116 colonies per well is counted using GelCount™ (Oxford Optronix Ltd.) and the raw data results are indicated in Table 6. The number of HCT-116 colonies per well is normalized to control treatment and this data is represented as % survival in FIG. 6.

What is claimed is:

1. A method of treating cancer, comprising administering to a patient in need of such treatment a combination of ((1R,2R,3S,4R)-2,3-dihydroxy-4-(2-(3-(trifluoromethyl-thio)phenyl)pyrazolo[1,5-a]pyrimidin-7-ylamino)cyclopentyl)methyl sulfamate (Compound 1) or a pharmaceutically acceptable salt thereof and radiation, wherein the cancer is selected from the group consisting of breast cancer, colorectal cancer, ovarian cancer, lung cancer, prostate cancer, head and neck cancer, gastric cancer, esophageal cancer, gastro-esophageal junction cancer, multiple myeloma, and non-Hodgkin's lymphoma; and wherein the radiation is particle radiation or administered by external beam radiation.

2. The method of claim 1, wherein the cancer is breast cancer, colorectal cancer, ovarian cancer, lung cancer, prostate cancer or head and neck cancer.

3. The method of claim 1, wherein the cancer is gastric cancer, esophageal cancer, or gastro-esophageal junction cancer.

4. The method of claim 1, wherein the cancer is multiple myeloma, or non-Hodgkin's lymphoma.

5. The method of claim 1, wherein the radiation is particle radiation.

6. The method of claim 1, wherein the radiation is administered by external beam-radiation.

7. The method of claim 1, wherein ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered on each of days 1 and 4 of each week repeated for 2 to 8 weeks.

8. The method of claim 1, wherein ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered on day 1 of each week repeated for 2 to 8 weeks.

9. The method of claim 1, wherein ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered on each of days 1-5 of each week repeated for 2 to 8 weeks.

10. The method of claim 1, wherein the radiation is administered on each of days 1-5 of each week repeated for 2 to 8 weeks.

11. The method of claim 1, wherein the radiation is administered on any two of days 1-5 of each week repeated for 5 to 8 weeks.

12. The method of claim 1, wherein ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered at a dose of about 4 mg to about 65 mg.

13. The method of claim 1, wherein ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered at a dose of about 15 mg to about 55 mg.

14. The method of claim 1, wherein ((1R,2R,3 S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered at a dose of about 18 mg to about 43 mg.

15. The method of claim 1, wherein the total dose of radiation administered is about 20 Gy to about 80 Gy.

16. The method of claim 1, wherein ((1R,2R,3S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered on each of days 1 and 4 of each week repeated for 6 to 8 weeks and wherein the radiation is administered on each of days 1-5 of each week repeated for 6 to 8 weeks.

17. The method of claim 1, wherein ((1R,2R,3 S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered on day 1 each week repeated for 6 to 8 weeks and wherein the radiation is administered on each of days 1-5 of each week repeated for 6 to 8 weeks.

18. The method of claim 1, wherein ((1R,2R,3 S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is administered on each of days 1-5 of each week repeated for 6 to 8 weeks and wherein the radiation is administered on each of days 1-5 of each week repeated for 6 to 8 weeks.

19. The method of claim 1, wherein ((1R,2R,3 S,4R)-2,3-dihydroxy-4-(2-(3-(trifluoromethylthio)phenyl)pyrazolo[1,5-a]pyrimidin-7-ylamino)cyclopentyl)methyl sulfamate (Compound 1) or a pharmaceutically acceptable salt thereof is not administered for any one or two week(s) of a 6-to-8-week period.

20. The method of claim 6, wherein the radiation is photon radiation.

* * * * *